(12) United States Patent
Brigham et al.

(10) Patent No.: US 11,647,965 B2
(45) Date of Patent: May 16, 2023

(54) BLOOD-PRESSURE-RELATED INFORMATION DISPLAY DEVICE, BLOOD-PRESSURE-RELATED INFORMATION DISPLAY METHOD, AND NON-TRANSITORY COMPUTER READABLE MEDIUM

(71) Applicants: OMRON CORPORATION, Kyoto (JP); OMRON HEALTHCARE CO., LTD., Muko (JP)

(72) Inventors: Brian Brigham, Kyoto (JP); Shusuke Eshita, Kyoto (JP)

(73) Assignees: OMRON CORPORATION, Kyoto (JP); OMRON HEALTHCARE CO., LTD., Muko (JP)

(*) Notice: Subject to any disclaimer, the term of this patent is extended or adjusted under 35 U.S.C. 154(b) by 569 days.

(21) Appl. No.: 16/454,745

(22) Filed: Jun. 27, 2019

(65) Prior Publication Data
US 2019/0313982 A1    Oct. 17, 2019

Related U.S. Application Data

(63) Continuation of application No. PCT/JP2017/042371, filed on Nov. 27, 2017.

(30) Foreign Application Priority Data

Dec. 28, 2016 (JP) .............................. JP2016-256035

(51) Int. Cl.
*A61B 5/00* (2006.01)
*A61B 5/021* (2006.01)
(Continued)

(52) U.S. Cl.
CPC ............ *A61B 5/7425* (2013.01); *A61B 5/021* (2013.01); *A61B 5/681* (2013.01); *A61B 5/7275* (2013.01);
(Continued)

(58) Field of Classification Search
CPC ....... A61B 5/7425; A61B 5/742; A61B 5/743; A61B 5/746; A61B 5/681; A61B 5/021;
(Continued)

(56) References Cited

U.S. PATENT DOCUMENTS 9,778,079 B1 * 10/2017 Al-Ali ................... G01D 13/06
9,875,560 B2 * 1/2018 Rajagopalan ......... G06T 11/203
(Continued)

FOREIGN PATENT DOCUMENTS

CN    101554322 A    10/2009
CN    102215744 A    10/2011
(Continued)

OTHER PUBLICATIONS

Jan. 23, 2018 International Search Report issued in International Patent Application No. PCT/JP2017/042371.
(Continued)

*Primary Examiner* — Matthew Kremer
*Assistant Examiner* — Kyle W. Kretzer
(74) *Attorney, Agent, or Firm* — Oliff PLC

(57) ABSTRACT

A blood-pressure-related information display device includes a data acquisition unit, a risk value calculator, and a display processor. The data acquisition unit acquires blood pressure data including a systolic blood pressure and a diastolic blood pressure for the subject. The risk value calculator obtains a systolic risk value representing a risk corresponding to the acquired systolic blood pressure and a diastolic risk value representing a risk corresponding to the acquired diastolic blood pressure based on a predetermined blood pressure standard. The display processor performs processing of displaying a risk range from the systolic risk value to the diastolic risk value in a curved or straight elongated display region defining a one-dimensional risk coordinate in the display screen.

12 Claims, 18 Drawing Sheets

(51) Int. Cl.
  *G16H 50/30* (2018.01)
  *A61B 5/022* (2006.01)
(52) U.S. Cl.
  CPC .......... *A61B 5/022* (2013.01); *A61B 5/02233* (2013.01); *A61B 5/746* (2013.01); *G16H 50/30* (2018.01)
(58) Field of Classification Search
  CPC ... A61B 5/7275; A61B 5/02233; A61B 5/022; A61B 5/339; G16H 50/30
  See application file for complete search history.

(56) References Cited

U.S. PATENT DOCUMENTS

| | | | | |
|---|---|---|---|---|
| 10,580,173 | B2* | 3/2020 | Rajagopalan | G16H 15/00 |
| 10,991,135 | B2* | 4/2021 | Al-Ali | A61B 5/742 |
| 2011/0218446 | A1* | 9/2011 | Maruta | A61B 5/02141 |
| | | | | 600/490 |
| 2013/0211214 | A1* | 8/2013 | Olsen | A61B 5/742 |
| | | | | 600/323 |
| 2014/0055285 | A1* | 2/2014 | Tesanovic | A61B 5/0022 |
| | | | | 340/870.09 |
| 2018/0042493 | A1* | 2/2018 | Muehlsteff | A61B 5/02141 |

FOREIGN PATENT DOCUMENTS

| | | |
|---|---|---|
| CN | 105848567 A | 8/2016 |
| JP | S62-197304 U | 12/1987 |
| JP | S64-19406 U | 1/1989 |
| JP | 2006-122144 A | 5/2006 |
| JP | 2010-119446 A | 6/2010 |
| WO | 2016/135043 A1 | 9/2016 |

OTHER PUBLICATIONS

May 28, 2021 Office Action issued in Chinese Patent Application No. 201780080642.9.
Oct. 18, 2021 Office Action issued in Chinese Patent Application No. 201780080642.9.

* cited by examiner

BLOOD PRESSURE CLASSIFICATION BY AMERICAN HEART ASSOCIATION (AHA)

| HYPERTENSIVE CATEGORY | SYSTOLIC BLOOD PRESSURE (MAXIMUM BLOOD PRESSURE) mmHg | | DIASTOLIC BLOOD PRESSURE (MINIMUM BLOOD PRESSURE) mmHg |
|---|---|---|---|
| NORMAL | LESS THAN 120 | AND | LESS THAN 80 |
| PREHYPERTENSION | 120 TO 139 | OR | 80 TO 89 |
| HYPERTENSIVE STAGE 1 | 140 TO 159 | OR | 90 TO 99 |
| HYPERTENSIVE STAGE 2 | HIGHER THAN OR EQUAL TO 160 | OR | HIGHER THAN OR EQUAL TO 100 |
| HYPERTENSIVE CRISIS (EMERGENCY TREATMENT IS REQUIRED) | HIGHER THAN 180 | OR | HIGHER THAN 110 |

FIG.9

BLOOD-PRESSURE-RELATED INFORMATION DISPLAY DEVICE, BLOOD-PRESSURE-RELATED INFORMATION DISPLAY METHOD, AND NON-TRANSITORY COMPUTER READABLE MEDIUM

CROSS-REFERENCE TO RELATED APPLICATIONS

The present application is a continuation application of International Application No. PCT/JP2017/042371, filed Nov. 27, 2017, which claims priority to Japanese Patent Application No. 2016-256035, filed Dec. 28, 2016. The contents of these applications are incorporated herein by reference in their entirety.

BACKGROUND OF THE INVENTION

Field of the Invention

The present invention relates to a blood-pressure-related information display device, a blood-pressure-related information display method, and a non-transitory computer-readable recording medium.

Discussion of the Background

Conventionally, as a device that displays the information related to the blood pressure of the subject, as disclosed in Japanese Utility Model Application Publication No. 64-19406, an indicator (display region) that indicates a scale of a blood pressure value and a blood pressure classification zone based on a World Health Organization (WHO) standard is provided along two concentric arcs having different diameters, the WHO blood pressure classification zone related to a maximum blood pressure (systolic blood pressure (SBP)) is indicated in the outer concentric circle, and the WHO blood pressure classification zone related to a minimum blood pressure (diastolic blood pressure (DBP)) is indicated in the inner concentric circle. In the indicator (display region), different colors are attached to four zones of a high blood pressure zone, a boundary high blood pressure zone, a normal zone, and a low blood pressure zone. Consequently, the blood pressure classification zone is easily identified.

SUMMARY OF THE INVENTION

According to a first aspect of the present disclosure, a blood-pressure-related information display device that displays information related to a blood pressure of a subject on a display screen, includes
a data acquisition unit to acquire blood pressure data including a systolic blood pressure and a diastolic blood pressure for the subject,
a risk value calculator to obtain a systolic risk value representing a risk corresponding to the acquired systolic blood pressure and a diastolic risk value representing a risk corresponding to the acquired diastolic blood pressure based on a predetermined blood pressure standard, and
a display processor to perform processing of displaying a risk range from the systolic risk value to the diastolic risk value in a curved or straight elongated display region defining a one-dimensional risk coordinate in the display screen.

According to a second aspect of the present disclosure, a blood-pressure-related information display method for displaying information related to a blood pressure of a subject on a display screen, the blood-pressure-related information display method, includes
acquiring blood pressure data including a systolic blood pressure and a diastolic blood pressure for the subject,
obtaining a systolic risk value representing a risk corresponding to the acquired systolic blood pressure and a diastolic risk value representing a risk corresponding to the acquired diastolic blood pressure based on a predetermined blood pressure standard, and
performing processing of displaying a risk range from the systolic risk value to the diastolic risk value in a curved or straight elongated display region defining a one-dimensional risk coordinate in the display screen.

According to a third aspect of the present disclosure, a non-transitory computer-readable recording medium storing program which, when executed by a computer, causes the computer to perform a blood-pressure-related information display method for displaying information related to a blood pressure of a subject on a display screen, the blood-pressure-related information display method includes
acquiring blood pressure data including a systolic blood pressure and a diastolic blood pressure for the subject,
obtaining a systolic risk value representing a risk corresponding to the acquired systolic blood pressure and a diastolic risk value representing a risk corresponding to the acquired diastolic blood pressure based on a predetermined blood pressure standard, and
performing processing of displaying a risk range from the systolic risk value to the diastolic risk value in a curved or straight elongated display region defining a one-dimensional risk coordinate in the display screen.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 9 is a view illustrating a classification published by the American Heart Association (AHA) as an example of a predetermined blood pressure standard.

DESCRIPTION OF THE EMBODIMENTS

Figure 1:
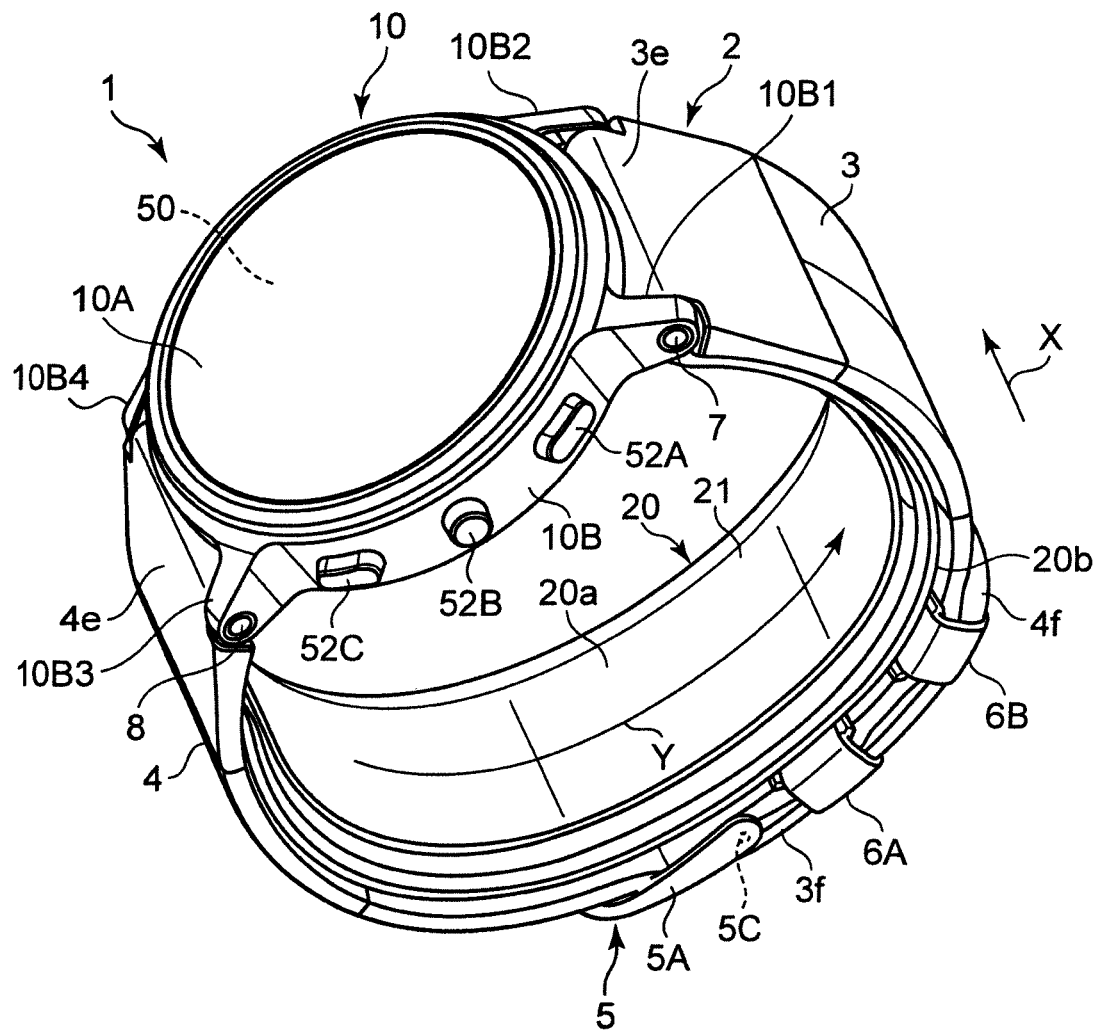
FIG. 1 is a view illustrating an external appearance of a sphygmomanometer according to an embodiment to which a blood-pressure-related information display device of the present embodiment is applied when the sphygmomanometer is obliquely viewed with a belt fastened.

The embodiments will now be described with reference to the accompanying drawings, wherein like reference numerals designate corresponding or identical elements throughout the various drawings.

Hereinafter, embodiments of the present invention will be described in detail with reference to the drawings.
(Configuration of Sphygmomanometer)

Figure 2:
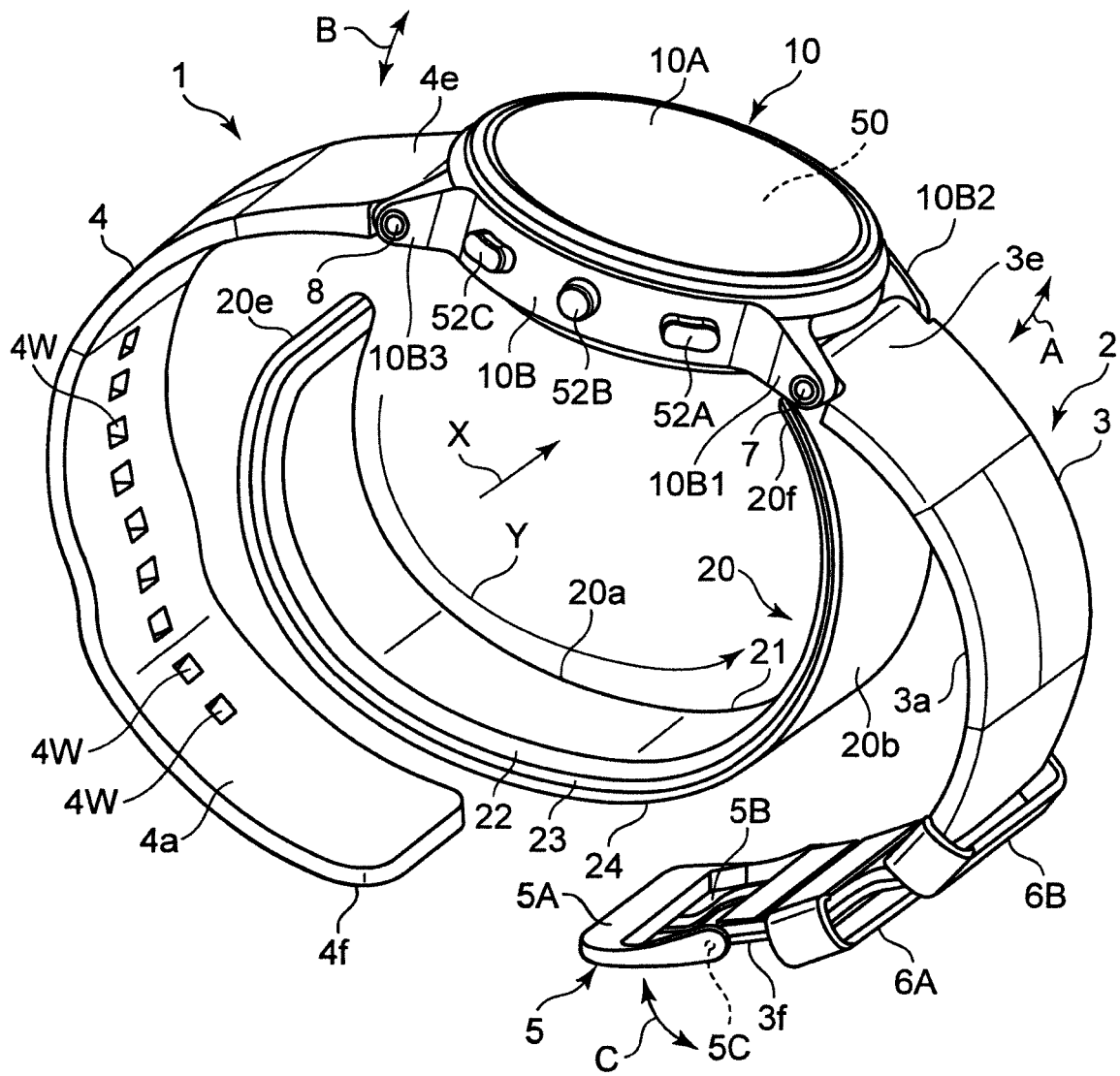
FIG. 2 is a view illustrating the external appearance of the sphygmomanometer when the sphygmomanometer is obliquely viewed with the belt opened.

FIG. 1 illustrates an external appearance of a sphygmomanometer (the whole is indicated by the reference numeral 1) according to an embodiment to which a blood-pressure-related information display device of the present embodiment of the invention is applied when the sphygmomanometer is obliquely viewed with a belt 2 fastened. FIG. 2 illustrates the external appearance of the sphygmomanometer 1 when the sphygmomanometer 1 is obliquely viewed with the belt 2 unfastened.

Figure 6A:
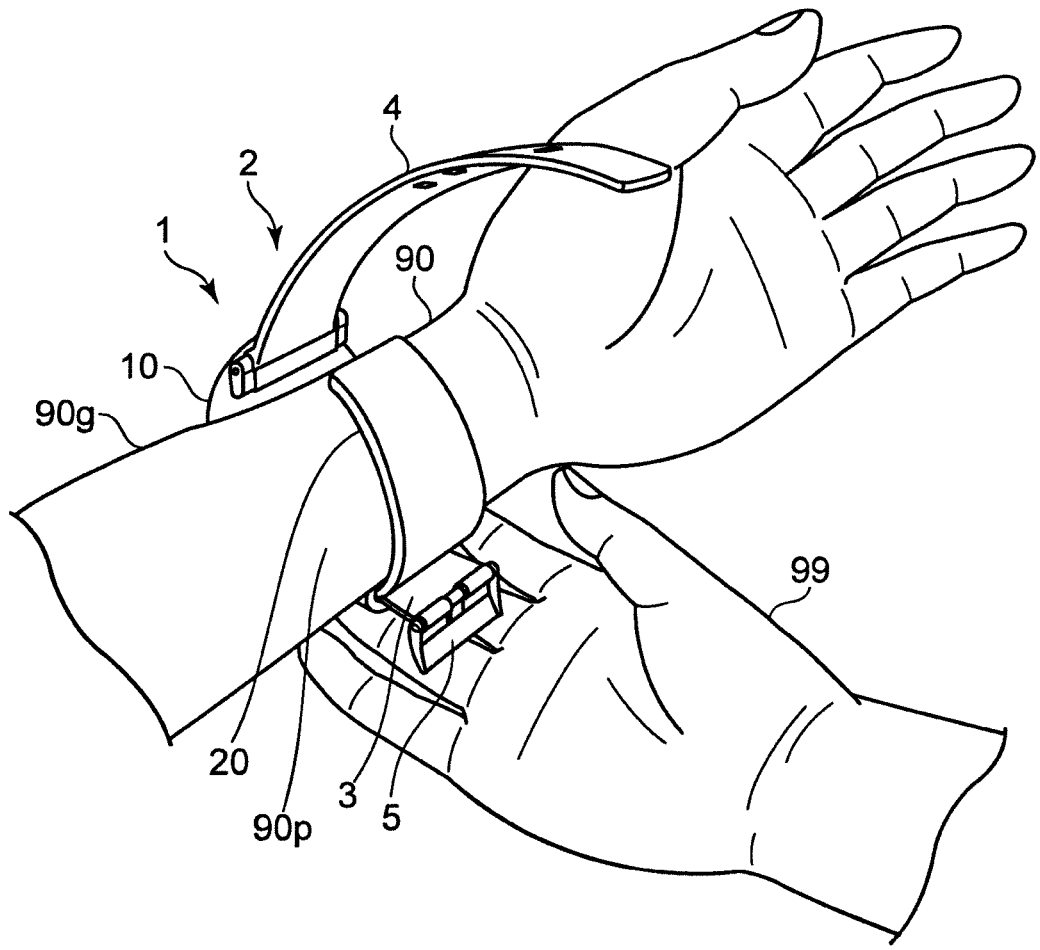
FIG. 6A is a perspective view illustrating a state in which the user wears a cuff structure on the left wrist using a right hand.
Figure 6B:
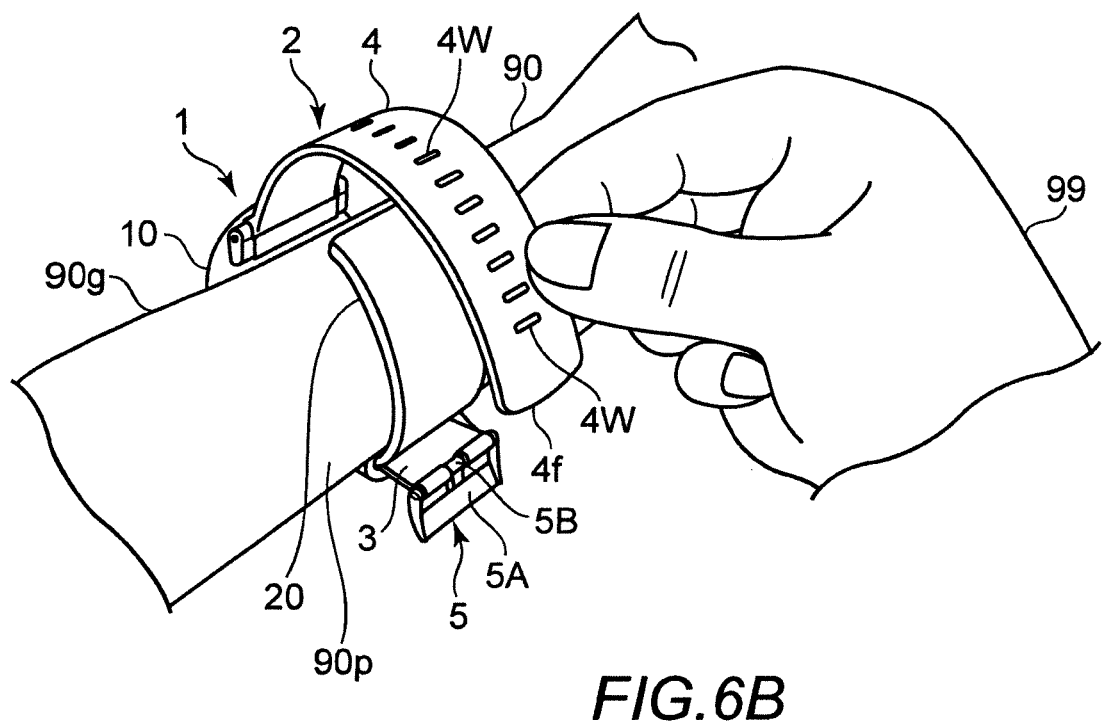
FIG. 6B is a perspective view illustrating a state in which the user uses the right hand to collectively bind the left wrist and the cuff structure with a belt.
Figure 6C:
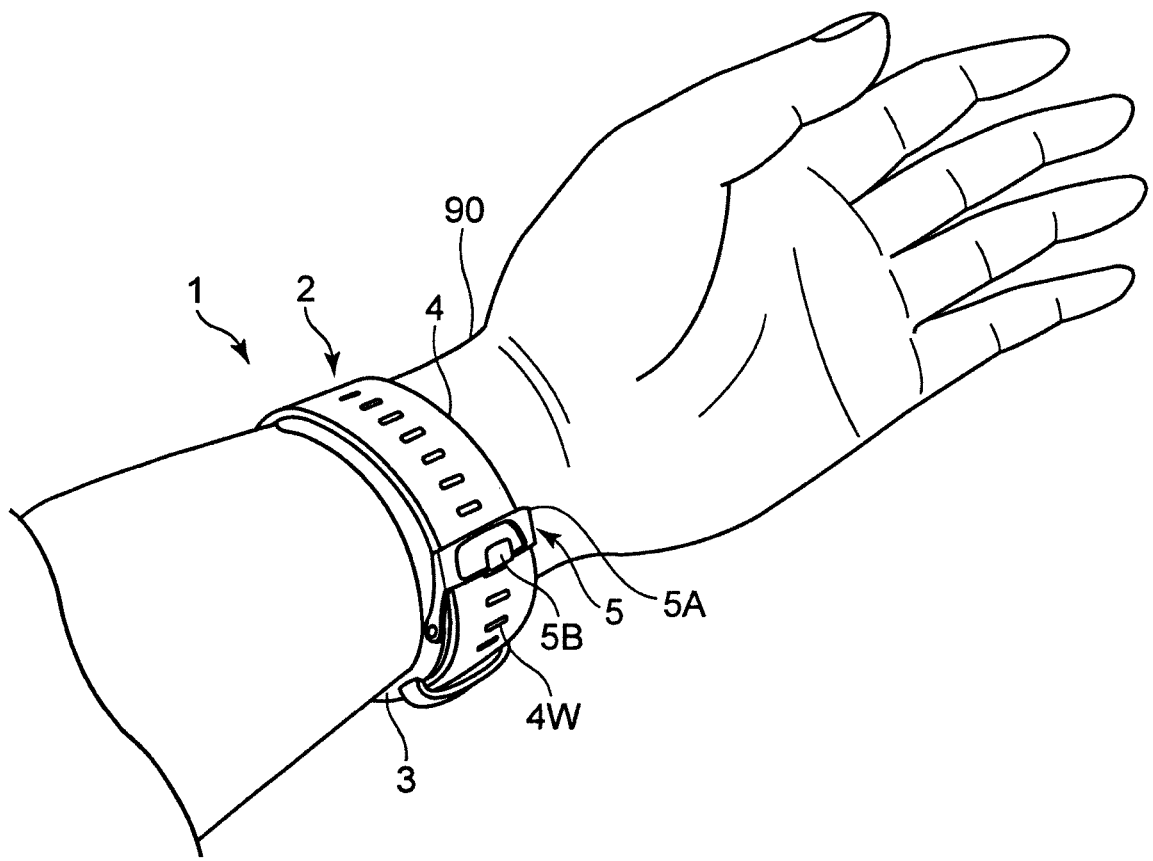
FIG. 6C is a perspective view illustrating a state in which the sphygmomanometer is attached to the left wrist of the user.

As illustrated in FIGS. 1 and 2, the sphygmomanometer 1 roughly includes a main body 10, the belt 2 that extends from the main body 10 to be worn while binding a measured site (in this example, as illustrated in FIG. 6C, a left wrist 90 is intended to be measured as the measured site), and a belt-shaped cuff structure 20 in which one end 20f is attached to the main body 10. In this example, a dimension in a width direction X of the belt 2 is set to 29 mm. In this example, a thickness of the belt 2 is set to 2 mm.

In this example, the main body 10 includes a case 10B having a substantially short cylindrical shape, a circular glass 10A attached to an upper portion (in FIGS. 1 and 2) of the case 10B, and a back lid (not illustrated) attached to a lower portion of the case 10B. Pairs of protruding lugs 10B1, 10B2 and 10B3, 10B4 (in FIGS. 1 and 2) on the left and right sides are integrally provided on side surfaces of the case 10B in order to attach the belt 2.

A display 50 constituting a display screen is provided in a glass 10A of the upper portion of case 10B. On the side surface of the front side (in FIGS. 1 and 2) of the main body 10, a measurement switch 52A that gives an instruction to start or stop blood pressure measurement, a home switch 52B that returns the display screen of the display 50 to a predetermined home screen, and a recording call switch 52C that instructs the display 50 to display a measurement record such as a blood pressure and an activity mass in the past are provided (these switches are collectively referred to as the operation unit 52). Also, inside the main body 10, a blood pressure measurement element including a pump 30 is mounted (to be described in detail later). In this example, the sphygmomanometer 1 includes the functions of an activity meter and a pulse monitor. The main body 10 is small and thin so as not to interfere with the daily activities of a user.

As can clearly be seen from FIG. 2, the belt 2 has a belt-shaped first belt 3 extending from the main body 10 to one side (right side in FIG. 2) in one direction and a belt-shaped second belt 4 extending from the main body 10 to the other side (left side in FIG. 2) in one direction. A root 3e of the first belt 3 on the side closer to the main body 10 is attached to the lugs 10B1, 10B2 of the main body 10 so as to be turnable as illustrated by a two-way arrow A about a connecting rod 7 (known spring rod) extending in a width direction X of the belt. Similarly, a root 4e of the second belt 4 on the side closer to the main body 10 is attached to the lugs 10B3, 10B4 of the main body 10 so as to be turnable as illustrated by a two-way arrow B about a connecting rod 8 (known spring rod) extending in the width direction X of the belt.

A tail lock 5 is attached to a leading end 3f of the first belt 3 on the side farther from the main body 10. The tail lock 5 is a known type, and includes a frame-shaped body 5A having a substantial U-shape, a prong 5B, and a connecting rod 5C extending in the width direction X of the belt. The frame-shaped body 5A and the prong 5B are attached to the leading end 3f of the first belt 3 on the side farther from the main body 10 so as to be turnable as indicated by a two-way arrow C about the connecting rod 5C. Between the leading end 3f and the root 3e of the first belt 3, ring-shaped belt holders 6A, 6B are integrally provided at a predetermined position with respect to a longitudinal direction (corresponding to a circumferential direction Y of the left wrist 90) of the first belt 3. An inner circumferential surface 3a of the first belt 3 does not protrude toward the inner circumferential side at places of the belt holders 6A, 6B, but is formed substantially flat (locally although it curved as a whole). Consequently, the belt 2 uniformly binds and restrains the outer circumferential side of the cuff structure 20.

A plurality of small holes 4w, 4w, . . . are made between the root 4e and the leading end 4f on the side farther from the main body 10 in the second belt 4 while being pierced in a thickness direction of the second belt 4. When the first belt 3 and the second belt 4 are fastened, a portion connected to the leading end 4f of the second belt 4 is passed through the frame-shaped body 5A of the tail lock 5, and the prong 5B of the tail lock 5 is inserted into one of the plurality of small holes 4w, 4w, . . . of the second belt 4. Consequently, the first belt 3 and the second belt 4 are fastened as illustrated in FIG. 1.

In this example, the first belt 3 and the second belt 4 constituting the belt 2 are made of a plastic material exhibiting flexibility in the thickness direction and substantial non-stretchability in the longitudinal direction (corresponding to the circumferential direction Y of the left wrist 90). Consequently, the belt 2 can easily bind and restrain the outer circumferential side of the cuff structure 20 during the wear, and assist compression of the left wrist 90 during the blood pressure measurement (to be described later). The first belt 3 and the second belt 4 may be made of a leather material. Although the frame-shaped body 5A and the prong 5B that constitute the tail lock 5 are made of a metal material in this example, the frame-shaped body 5A and the prong 5B may be made of a plastic material.

As illustrated in FIG. 2, the cuff structure 20 includes a curler 24 disposed at an outermost circumference, a pressing cuff 23 disposed along the inner circumferential surface of the curler 24, a backboard 22 that is a reinforcing plate disposed along the inner circumferential surface of the pressing cuff 23, and a sensing cuff 21 disposed along the inner circumferential surface of the backboard 22.

Each of the curler 24, the pressing cuff 23, the backboard 22, and the sensing cuff 21 has an elongated belt shape in one direction (Y direction).

The sensing cuff 21 is formed into a bag shape. A flexible tube 38 (see FIG. 3) that supplies a pressure transmitting fluid (in this example, air) to the sensing cuff 21 or discharges the pressure transmitting fluid from the sensing cuff 21 is provided at an end of the root side (+Y side) with respect to the longitudinal direction Y of the sensing cuff 21. An inner circumferential surface 20a of the cuff structure 20 is constructed with the sensing cuff 21.

The pressing cuff 23 is also formed into a bag shape. A flexible tube 39 (see FIG. 3) that supplies the pressure transmitting fluid (in this example, air) to the pressing cuff 23 or discharges the pressure transmitting fluid from the pressing cuff 23 is provided at the end of the root side (+Y side) with respect to the longitudinal direction Y of the pressing cuff 23. When receiving the supply of the pressurizing fluid from the side of the main body 10 through the flexible tube 39 in the worn state, the pressing cuff 23 is inflated to press the left wrist 90.

Figure 5:
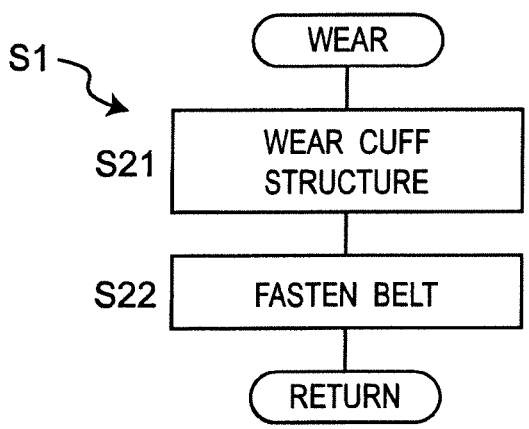
FIG. 5 is a flowchart illustrating processing in which the user wears the sphygmomanometer on a left wrist.

In this example, the backboard 22 is made of a plate-shaped resin (in this example, polypropylene) having a thickness of about 1 mm. The backboard 22 acts as a reinforcing plate, and can transmit the pressing force from the pressing cuff 23 to the entire region in the longitudinal direction Y of the sensing cuff 21 (corresponding to the circumferential direction of the left wrist 90). In the backboard 22, a plurality of V-shaped or U-shaped grooves in a section (not illustrated) extending in the width direction X are provided in parallel while separated from each other in the longitudinal direction Y. Consequently, the backboard 22 is thinned at the groove place compared to other portions, and is easy to bend. Thus, when the user collectively binds the left wrist 90 and the cuff structure 20 with the belt 2 during the wear (step S22 in FIG. 5), the backboard 22 does not prevent the cuff structure 20 from being curved along the circumferential direction Y of the left wrist 90.

In this example, the curler 24 is made of a resin plate (in this example, polypropylene) having the thickness of about 1 mm and a certain degree of flexibility and hardness. In a natural state, the curler 24 has a curved shape along the circumferential direction Y surrounding the left wrist 90. Consequently, the shape in the natural state of the cuff structure 20 is kept curved along the circumferential direction Y of the left wrist 90 as illustrated in FIG. 2.

One end 20f (a root of the curler 24) of the cuff structure 20 is attached to the main body 10. The other end 20e of the cuff structure 20 is a free end. As a result, the cuff structure 20 can be separated from the inner circumferential surfaces 3a, 4a of the belt 2.

Figure 3:
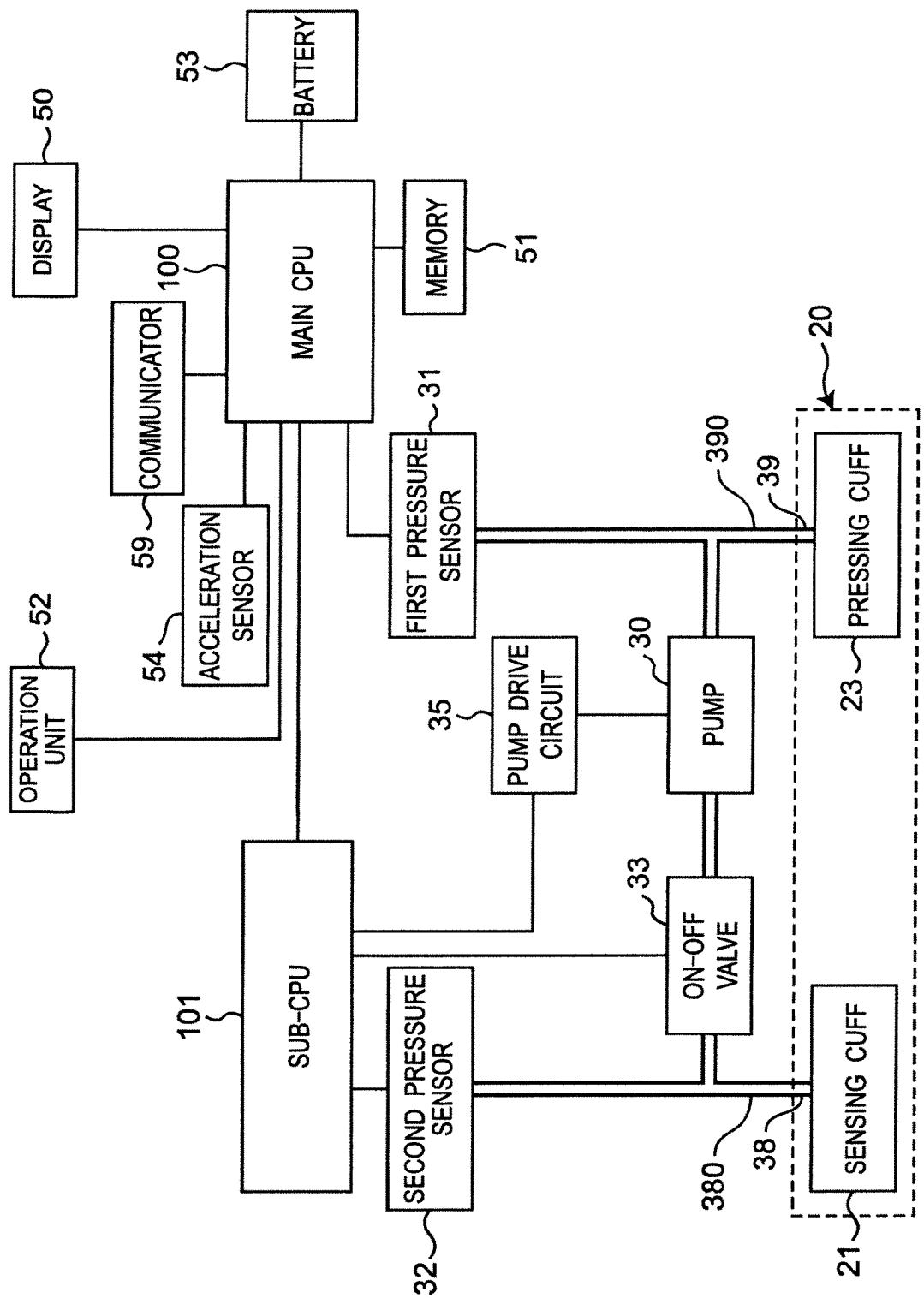
FIG. 3 is a view illustrating a block configuration of a control system of the sphygmomanometer.

FIG. 3 illustrates a block configuration of a control system of the sphygmomanometer 1. In addition to the display 50 and the operation unit 52, a main Central Processing Unit (CPU) 100 as a control unit, a sub-CPU 101, a memory 51 as a storage, an acceleration sensor 54, a communicator 59, a battery 53, a first pressure sensor 31 that detects pressure of the pressing cuff 23, a second pressure sensor 32 that detects pressure of the sensing cuff 21, a pump 30, an on-off valve 33, and a pump drive circuit 35 that drives the pump 30 are mounted as the blood pressure measurement element that performs the blood pressure measurement in the main body 10 of the sphygmomanometer 1. The main CPU 100 mainly controls the operation of the entire sphygmomanometer 1, and the sub-CPU 101 mainly controls the operation of an air system. Hereinafter, for convenience, the main CPU 100 and the sub-CPU 101 will be simply referred to as the CPU 100 in combination.

The display 50 is constructed with a Liquid Crystal Display (LCD) in this example, and displays information related to the blood pressure measurement such as a blood pressure measurement result and other information according to a control signal from the CPU 100. The display 50 is not limited to the organic EL display, but may be constructed with another type of display 50 such as an organic Electro Luminescence (EL) display. The display 50 may include a Light Emitting Diode (LED). The configuration of the display screen of the display 50 will be described later.

As described above, the operation unit 52 includes the measurement switch 52A that gives an instruction to start or stop the blood pressure measurement, the home switch 52B that returns the display screen of the display 50 to the predetermined home screen, and the recording call switch 52C that instructs the display 50 to display the measurement record such as the blood pressure and the activity mass in the past. In this example, these switches 52A to 52C are constructed with push switches, and input an operation signal to the CPU 100 in response to the instruction such as the start or stop of the blood pressure measurement from the user. The operation unit 52 is not limited to the push switch, but may be constructed with, for example, a pressure-sensitive (resistive) or proximity (electrostatic capacitive) touch panel switch. A microphone (not illustrated) may be provided to input the instruction to start the blood pressure measurement by user's voice.

The memory 51 non-transiently stores data of a program controlling the sphygmomanometer 1, data used to control the sphygmomanometer 1, setting data setting various functions of the sphygmomanometer 1, data of the measurement result of the blood pressure value, and the like. The memory 51 is also used as a work memory or the like when a program is executed.

The CPU 100 performs various functions as a controller according to the program controlling the sphygmomanometer 1 stored in the memory 51. For example, when performing the blood pressure measurement function, the CPU 100 controls drive of the pump 30 and the on-off valve 33 based on the signals from the first pressure sensor 31 and the second pressure sensor 32 in response to the instruction to start the blood pressure measurement from the measurement switch 52A of the operation unit 52. The CPU 100 controls the calculation of the blood pressure value, a pulse, and the like based on a signal from the second pressure sensor 32.

The acceleration sensor 54 is constructed with a three-axis acceleration sensor integrally incorporated in the main body 10. The acceleration sensor 54 outputs an acceleration signal representing the acceleration of the main body 10 in three directions orthogonal to one another to the CPU 100. In this example, the output of the acceleration sensor 54 is used to measure the activity mass.

The communicator 59 is controlled by the CPU 100 to transmit predetermined information to an external device through the network, and to receive information from the external device through the network to deliver the information to the CPU 100. The communication through the network may be conducted in a wireless or wired manner. In this embodiment, the network is the Internet. However, the network is not limited to the Internet, but may be another type of network such as an in-hospital LAN (Local Area Network) or one-to-one communication using a USB cable or the like. The communicator 59 may include a micro USB connector.

In this example, the battery 53 is constructed with a rechargeable secondary battery. The battery 53 supplied power to an element mounted on the main body 10, in this example, each of the elements including the CPU 100, the memory 51, the acceleration sensor 54, the communicator 59, the first pressure sensor 31, the second pressure sensor 32, the pump 30, the on-off valve 33, and the pump drive circuit 35.

The pump 30 is constructed with a piezoelectric pump in this example, and is driven by the pump drive circuit 35 based on a control signal supplied from the CPU 100. The pump 30 is connected to the pressing cuff 23 through a first flow path forming member 390 and a flexible tube 39, which constitute a first flow path, so as to be able to pass the fluid to the pressing cuff 23. The pump 30 can supply air as the pressurizing fluid to the pressing cuff 23 through the first flow path forming member 390 and the flexible tube 39. An exhaust valve (not illustrated) in which opening and closing are controlled according to on and off of the pump 30 is mounted on the pump 30. That is, the exhaust valve closes to assist sealing of the air in the pressing cuff 23 when the pump 30 is turned on, and the exhaust valve opens to discharge the air in the pressing cuff 23 to atmosphere through the flexible tube 39 and the first flow path forming member 390 when the pump 30 is turned off. The exhaust valve has a function of a check valve, and the air to be discharged does not flow backward.

The pump 30 is connected to the sensing cuff 21 through a second flow path forming member 380 and a flexible tube 38, which constitute a second flow path, so as to be able to pass the fluid to the sensing cuff 21. An on-off valve (in this example, a normally open electromagnetic valve) 33 is interposed in the second flow path (in fact, between the first flow path forming member 390 and the second flow path forming member 380). The opening and closing (opening degree) of the on-off valve 33 is controlled based on a control signal supplied from the CPU 100. When the on-off valve 33 is in the open state, the air can be supplied and stored as the pressure transmitting fluid from the pump 30 to the sensing cuff 21 through the second flow path.

In this example each of the first pressure sensor 31 and the second pressure sensor 32 is constructed with a piezoresistive pressure sensor. The first pressure sensor 31 detects the pressure in the pressing cuff 23 through the first flow path forming member 390 and the flexible tube 39 that constitute the first flow path. The second pressure sensor 32 detects the pressure in the sensing cuff 21 through the second flow path forming member 380 and the flexible tube 38 that constitute the second flow path.

The compact sphygmomanometer 1 is miniaturized and configured integrally by mounting the above blood pressure measurement element on the main body 10. Thus, the sphygmomanometer 1 is convenient for the user.

(Operation of Blood Pressure Measurement)

Figure 4:
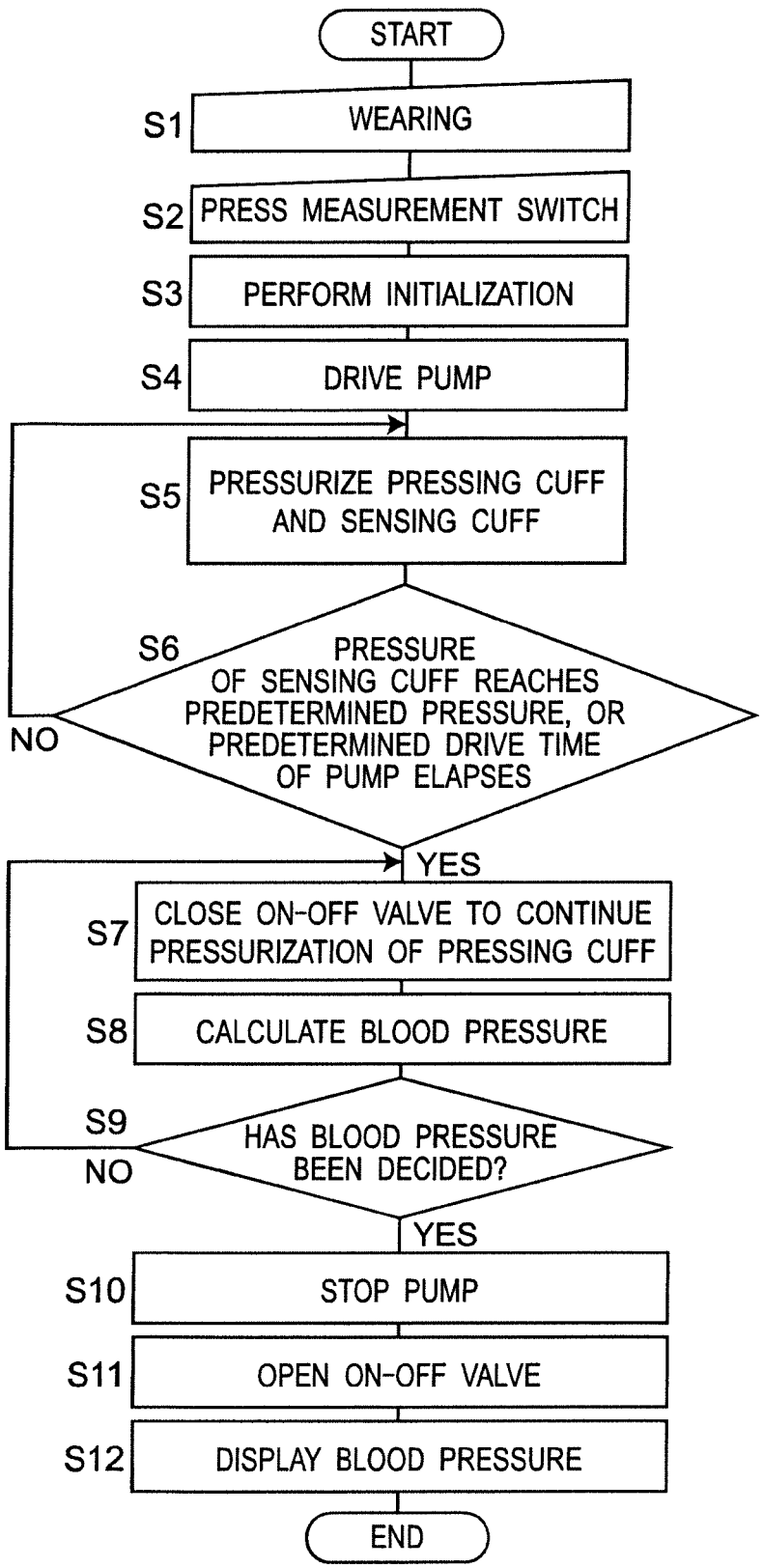
FIG. 4 is a flowchart illustrating an operation when a user performs blood pressure measurement with the sphygmomanometer.

FIG. 4 is a flowchart illustrating an operation when the user acts as a subject to perform the blood pressure measurement with the sphygmomanometer 1.

As illustrated in step S1 of FIG. 4, the user wears the sphygmomanometer 1 on the left wrist 90 as the measured site. As illustrated in FIG. 6A, the user wears the cuff structure 20 on the left wrist 90 using a right hand 99 (step S21 in FIG. 5). The user disposes the main body 10 of the sphygmomanometer 1 on a back side surface (a surface on the back of the hand) 90g of the left wrist 90. At this point, in the natural state, the cuff structure 20 is curved along the circumferential direction Y of the left wrist 90 by the curler 24. Thus, in this example, the user fits the cuff structure 20 in the outer circumferential surface of the left wrist 90 using the hand (in this example, the right hand 99) of a right half body on the opposite side of a left half body on the side to which the left wrist 90 belongs, which allows the cuff structure 20 to be easily worn on the left wrist 90. In the state in which the cuff structure 20 is worn on the left wrist 90, the cuff structure 20 grips the left wrist 90 even if the user releases the right hand 99 from the cuff structure 20, so that the cuff structure 20 (and the belt 2 and the main body 10) hardly comes off from the left wrist 90.

Subsequently, as illustrated in FIG. 6B, the user collectively bonds the left wrist 90 and the cuff structure 20 with the belt 2 using the right hand 99. Specifically, a portion connected to the leading end 4f of the second belt 4 is passed through the frame-shaped body 5A of the tail lock 5 of the first belt 3, and the prong 5B of the tail lock 5 is inserted into one of the plurality of small holes 4w, 4w, . . . of the second belt 4. Consequently, as illustrated to FIG. 6C, the first belt 3 and the second belt 4 are fastened (step S22 in FIG. 5). Consequently, the belt 2 extending from the main body 10 binds the left wrist 90, and the belt-shaped cuff structure 20 in which the one end 20f is attached to the main body 10 is disposed on the inner circumferential side closer to the left wrist 90 than the belt 2.

In the sphygmomanometer 1, the cuff structure 20 can be separated from the inner circumferential surfaces 3a, 4a of the belt 2, and the other end 20e on the opposite side of the one end 20f of the cuff structure 20 becomes a free end. Thus, when the first belt 3 and the second belt 4 are fastened, the cuff structure 20 receives inward force from the belt 2, and the cuff structure 20 can be slid or deformed just along the outer circumferential surface of the left wrist 90. Consequently, in the wear state, the cuff structure 20 and the belt 2 are in close contact with the outer circumferential surface of the left wrist 90 in this order, namely, the left wrist 90 is bound into the belt shape as a whole. In this way, the sphygmomanometer 1 can easily be worn on the left wrist 90.

Figure 7:
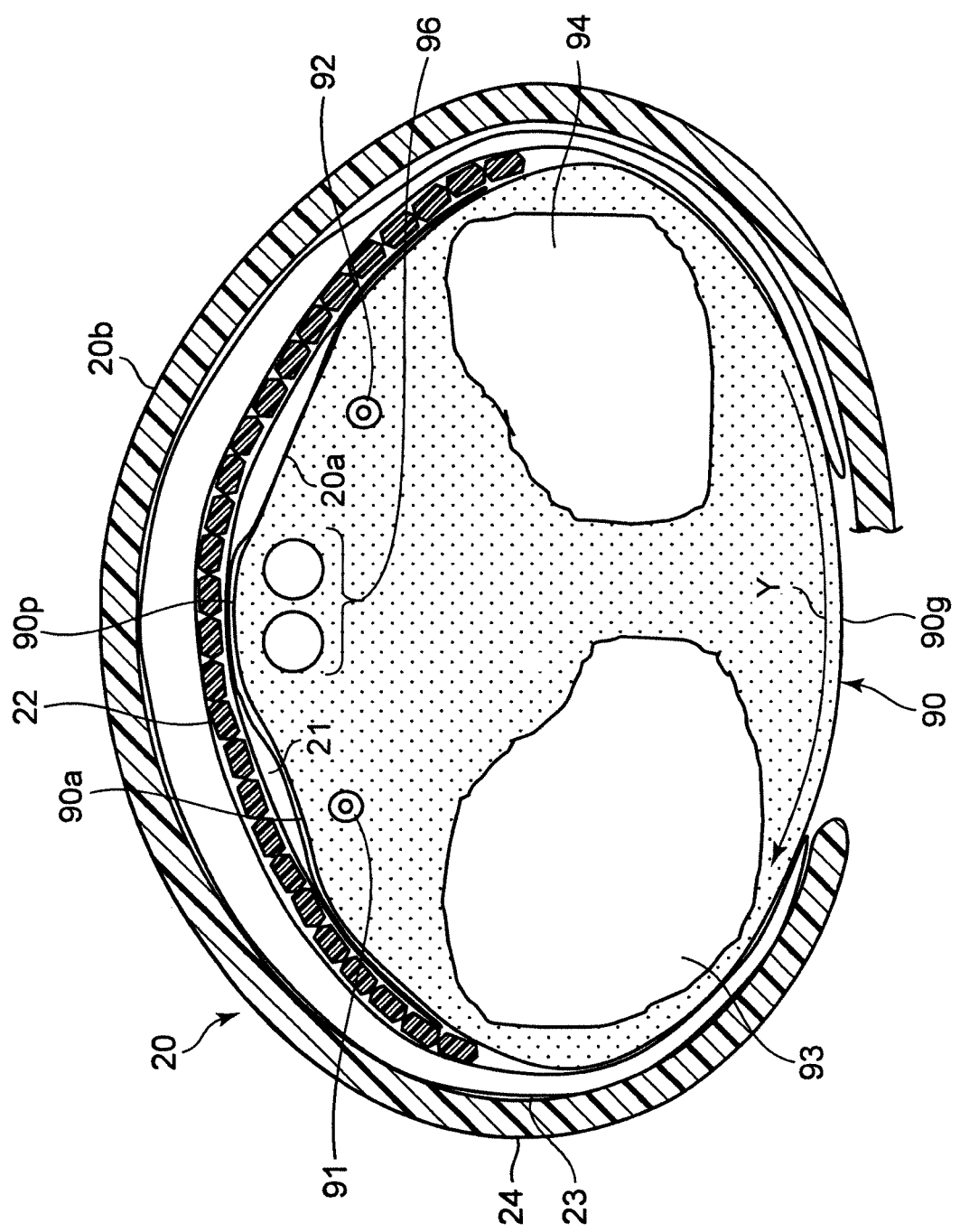
FIG. 7 is a view illustrating a section perpendicular to the left wrist of the user while the sphygmomanometer is attached to the left wrist of the user.

Specifically, as illustrated in FIG. 7, in the wear state, the bag-shaped pressing cuff 23 extends along the circumferential direction Y of the left wrist 90 on the inner circumferential side of the curler 24 included in the cuff structure 20. The bag-shaped sensing cuff 21 included in the cuff structure 20 is disposed on the inner circumferential side with respect to the pressing cuff 23 to contact with the palm side surface (a surface on the palm side of the hand) 90p of the left wrist 90, and extends in the circumferential direction Y so as to cross an artery passage portion 90a of the left wrist 90. The backboard 22 included in the cuff structure 20 is interposed between the pressing cuff 23 and the sensing cuff 21, and extends along the circumferential direction Y of the left wrist 90. The main body 10 and the belt 2 are not illustrated in FIG. 7. A radius 93, an ulna 94, a radial artery 91, an ulnar artery 92, and a tendon 96 of the left wrist 90 are illustrated in FIG. 7.

When the user presses the measurement switch 52A of the operation unit 52 provided in the main body 10 (step S2 in FIG. 4), the CPU 100 initializes a processing memory area (step S3 in FIG. 4). The CPU 100 turns off the pump 30 through the pump drive circuit 35 to open the exhaust valve built in the pump 30, and maintains the on-off valve 33 in the open state to discharge the air in the pressing cuff 23 and the sensing cuff 21. Subsequently, adjustment of 0 mmHg of the first pressure sensor 31 and the second pressure sensor 32 is controlled.

Subsequently, the CPU 100 acts as a pressurization controller and a fluid storage controller to turn on the pump 30 through the pump drive circuit 35 (step S4 in FIG. 4), and maintains the on-off valve 33 in the open state to start the pressurization of the pressing cuff 23 and the sensing cuff 21 (step S5 in FIG. 4). In a pressurization process, the pump 30 is driven through the pump drive circuit 35 while the pressures of the pressing cuff 23 and the sensing cuff 21 are monitored by the first pressure sensor 31 and the second pressure sensor 32, respectively. Consequently, the control is performed such that the air is sent to the pressing cuff 23 through the first flow path (the first flow path forming member 390 and the flexible tube 39), and such that the air is sent to the sensing cuff 21 through the second flow path (the second flow path forming member 380 and the flexible tube 38).

Subsequently, in step S6 of FIG. 4, the CPU 100 acts as the fluid storage controller to determine whether the pressure of the sensing cuff 21 has reached a predetermined pressure (in this example, 15 mmHg) or whether a predetermined drive time of the pump 30 has elapsed (in this example, 3 seconds). The reason the determination is made is that it is required to check whether an appropriate amount of air has been stored in the sensing cuff 21. When the negative determination is made in step S6 of FIG. 4, the processing waits until the pressure of the sensing cuff 21 reaches a predetermined pressure or the predetermined drive time of the pump 30 elapses. The "appropriate amount" of pressure transmitting fluid stored in the sensing cuff 21 is previously set on the basis of an experiment.

When the affirmative determination is made in step S6 of FIG. 4, it is determined that the appropriate amount of air has been stored in the sensing cuff 21. In step S7 of FIG. 4, the CPU 100 acts as the pressurization controller, closes the on-off valve 33, and continues the control of supplying the air from the pump 30 to the pressing cuff 23 through the first flow path. Consequently, the pressing cuff 23 is inflated and the pressure is gradually applied to press the left wrist 90. At this point, the backboard 22 transmits the pressing force from the pressing cuff 23 to the sensing cuff 21. The sensing cuff 21 presses the left wrist 90 (including the artery passage portion 90a). In the pressurization process, the CPU 100 monitors the pressure of the sensing cuff 21, namely, the pressure of the artery passage portion 90a of the left wrist 90 using the second pressure sensor 32 in order to calculate the blood pressure value, and acquire a pulse wave signal as a fluctuation component.

Subsequently, in step S8 of FIG. 4, the CPU 100 acts as a blood pressure calculator, and applies a known algorithm by an oscillometric method to try to calculate the blood pressure value (a systolic blood pressure SBP and a diastolic blood pressure DBP) based on the pulse wave signal acquired at this time.

At this point, when the blood pressure value cannot be calculated because of insufficient data (NO in step S9), the pieces of processing in steps S7 to S9 are repeated as long as the cuff pressure does not reach an upper limit pressure (for safety, for example, 300 mmHg is previously decided).

When the blood pressure value can be calculated (YES in step S9), the CPU 100 stops the pump 30 (step S10), opens the on-off valve 33 (step S11), and performs the control of discharging the air in the pressing cuff 23 and the sensing cuff 21. Finally, a measurement result of the blood pressure value is displayed on the display 50 (step S12). The processing of displaying the measurement result on the display screen of the display 50 will be described later.

The blood pressure calculation may be performed in not the pressurization process of the pressing cuff 23 but a decompression process.

As described above, in the sphygmomanometer 1, the air is stored in the sensing cuff 21 every time the blood pressure is measured, and the second pressure sensor 32 detects the pressure of the sensing cuff 21, namely, the pressure itself of the artery passage portion 90a of the left wrist 90 separately from the pressing cuff 23. Thus, as a result of setting of a smaller dimension (for example, about 25 mm) in the width direction X of the belt 2 and the cuff structure 20 (hereinafter, simply collectively referred to as a "cuff"), the blood pressure can accurately be measured even if the pressing cuff 23 is largely inflated in the thickness direction to generate a compression loss during the pressurization. In the wear state, the sensing cuff 21 extends in the circumferential direction Y so as to cross the artery passage portion 90a of the left wrist 90. Thus, when the user actually wears the sphygmomanometer 1 on the left wrist 90, even if the cuff is displaced to some extent in the circumferential direction Y of the left wrist 90 along with the main body 10, the sensing cuff 21 does not come off from the artery passage portion 90a of the left wrist 90. Thus, the blood pressure measurement value can be prevented from varying with respect to the actual blood pressure, and resultantly the blood pressure can accurately be measured.

In the above example, each time the blood pressure is measured, the air as the pressure transmitting fluid is stored in the sensing cuff 21, and the air is discharged after the measurement is completed. However, the present embodiment of the invention is not limited to the above example. The pressure transmitting fluid may be stored in the sensing cuff 21 and sealed at a manufacturing stage of the sphygmomanometer 1.

In the sphygmomanometer 1, the CPU 100 calculates and acquires the pulse (the number of times per minute) (/min) of the subject based on the above pulse wave signal in addition to the blood pressure value.

(Configuration of Display Screen of Display)

Figure 11:
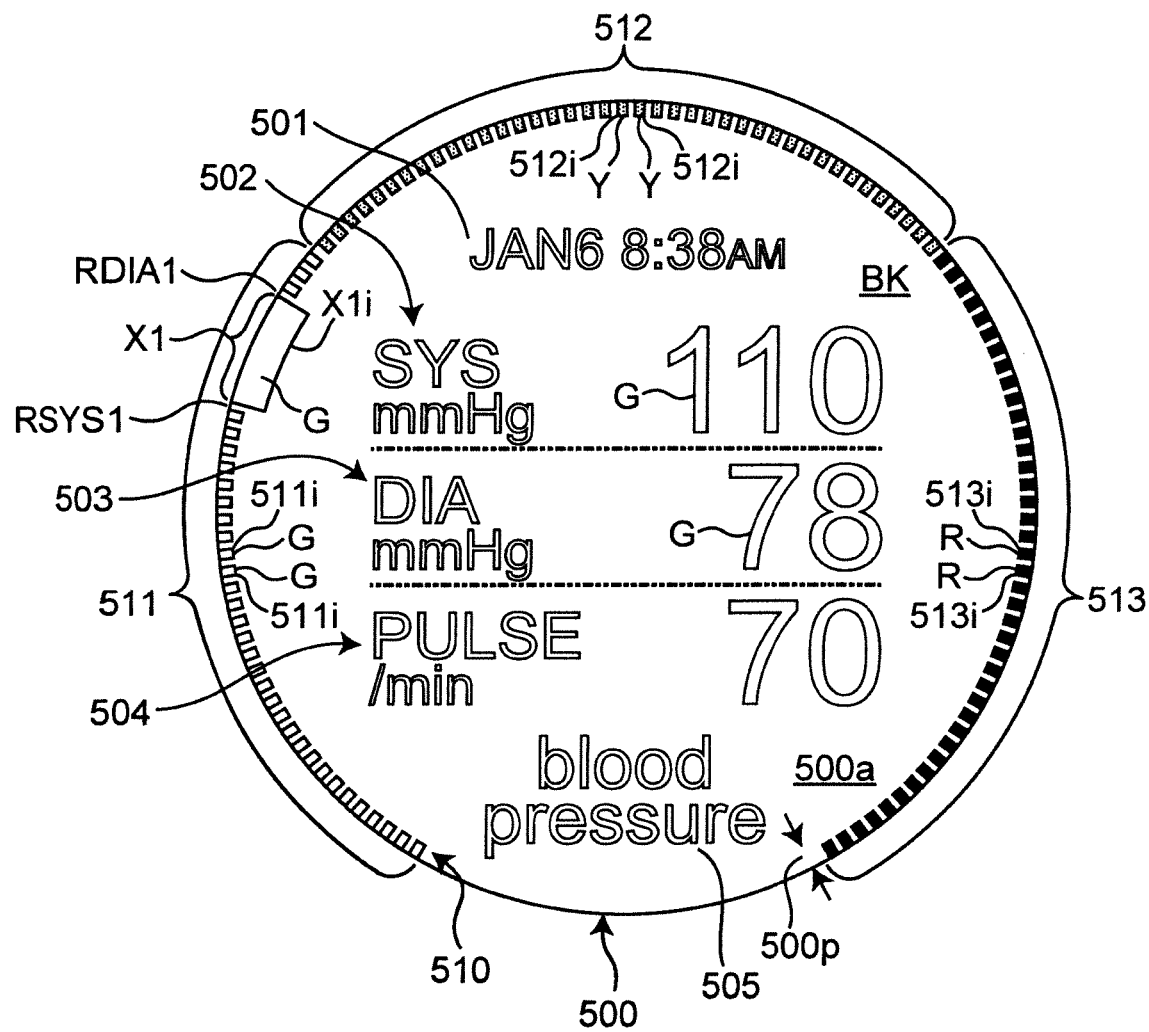
FIG. 11 is a view illustrating a first example of blood pressure risk display by the flowchart in FIG. 8.

FIG. 11 illustrates a configuration of a display screen 500 of the display 50. In this example, the display screen 500 has a circular outline. A current day and time display region 501 where current month, day, and time (in this example, "JAN6 8:38 AM" representing 8:38 AM, January 6) are displayed, a systolic blood pressure display region 502 where the systolic blood pressure (maximum blood pressure; SYS) is digitally displayed in mmHg units, and a diastolic blood pressure display region 503 where the diastolic blood pressure (minimum blood pressure) is digitally displayed in mmHg units, a pulse display region 504 where the pulse (PULSE) is digital displayed in units of the number of times (/min), and a title display region 505 where a title (in this example, "blood pressure") of the display screen 500 is represented are provided in an order from the upper stage to the lower stage in an internal region 500a (except for the annular circumferential edge 500p) of the display screen 500. Character strings "SYS mmHg", "DIA mmHg", PULSE/min indicating a meaning of a display content are displayed in a left half of the systolic blood pressure display region 502, a left half of the diastolic blood pressure display region 503, and a left half of the pulse display region 504, respectively. In this example, digital values "110", "78", and "70" are displayed in a right half of the systolic blood pressure display region 502, a right half of the diastolic blood pressure display region 503, and a right half of the pulse display region 504, respectively. In this example, a ground color BK of the internal region 500a is white or black.

In this example, an arc-shaped region (a region having a scale) 510 along the annular circumferential edge 500p is set in the display screen 500 as a curved elongated display region defining a one-dimensional risk coordinate.

The arc-shaped region 510 is divided into a plurality of stages along the arc, in this example, three stages of a first risk stage 511 to a third risk stage 513, according to a predetermined blood pressure standard.

In this example, a classification (hereinafter, referred to as "AHA classification") announced by the American Heart Association (AHA) as illustrated in FIG. 9 is used as the blood pressure standard. The first risk stage 511 corresponds to a "normal" category of the AHA classification. The second risk stage 512 includes "prehypertension" and "hypertension stage 1" of the AHA classification. The third risk stage 513 includes "hypertension stage 2" and "hypertensive crisis" of the AHA classification. The "normal" category of the AHA classification is the case that the systolic blood pressure (maximum blood pressure) is less than 120 mmHg and the diastolic blood pressure (minimum blood pressure) is less than 80 mmHg. The "prehypertension" is the case that the systolic blood pressure ranges from 120 mmHg to 139 mmHg or the diastolic blood pressure ranges from 80 mmHg to 89 mmHg. The "hypertensive stage 1" is the case that the systolic blood pressure ranges from 140 mmHg to 159 mmHg or the diastolic blood pressure ranges from 90 mmHg to 99 mmHg. The "hypertension stage 2" is the case that the systolic blood pressure is higher than or equal to 160 mmHg or the diastolic blood pressure is higher than or equal to 100 mmHg. The "hypertensive crisis" is the case that the systolic blood pressure is higher than 180 mmHg or the diastolic blood pressure is higher than 110 mmHg.

The first risk stage 511 of the arc-shaped region 510 in FIG. 11 is configured while a plurality of substantially rectangular scales 511$i$, 511$i$, . . . to each of which a green G is attached are arranged at a constant pitch along the circumferential edge 500p of the display screen 500. A gap exists between a certain scale 511$i$ and a scale 511$i$ adjacent thereto, and the ground color BK of the display screen 500 can be seen.

The second risk stage 512 of the arc-shaped region 510 is configured while a plurality of substantially rectangular scales 512$i$, 512$i$, . . . to each of which a yellow Y is attached are arranged at a constant pitch along the circumferential edge 500p of the display screen 500. Similarly to the first risk stage 511, a gap exists between a scale 512$i$ and a scale 512$i$ adjacent thereto, and the ground color BK of the display screen 500 can be seen.

The third risk stage 513 of the arc-shaped region 510 is configured while a plurality of substantially rectangular scales 512$i$, 513$i$, . . . to each of which a red R is attached are arranged at a constant pitch along the circumferential edge 500p of the display screen 500. Similarly to the first risk stage 511 and the second risk stage 512, a gap exists between a certain scale 513$i$ and a scale 513$i$ adjacent thereto, and the ground color BK of the display screen 500 can be seen.

The green G, the yellow Y, and the red R of three stages of the first to third risk stages 511 to 513 are set as colors that intuitively represent the meaning of safety (or relief), attention, and warning, respectively.

(Display Processing of Displaying Measurement Result on Display Screen of Display)

Figure 8:
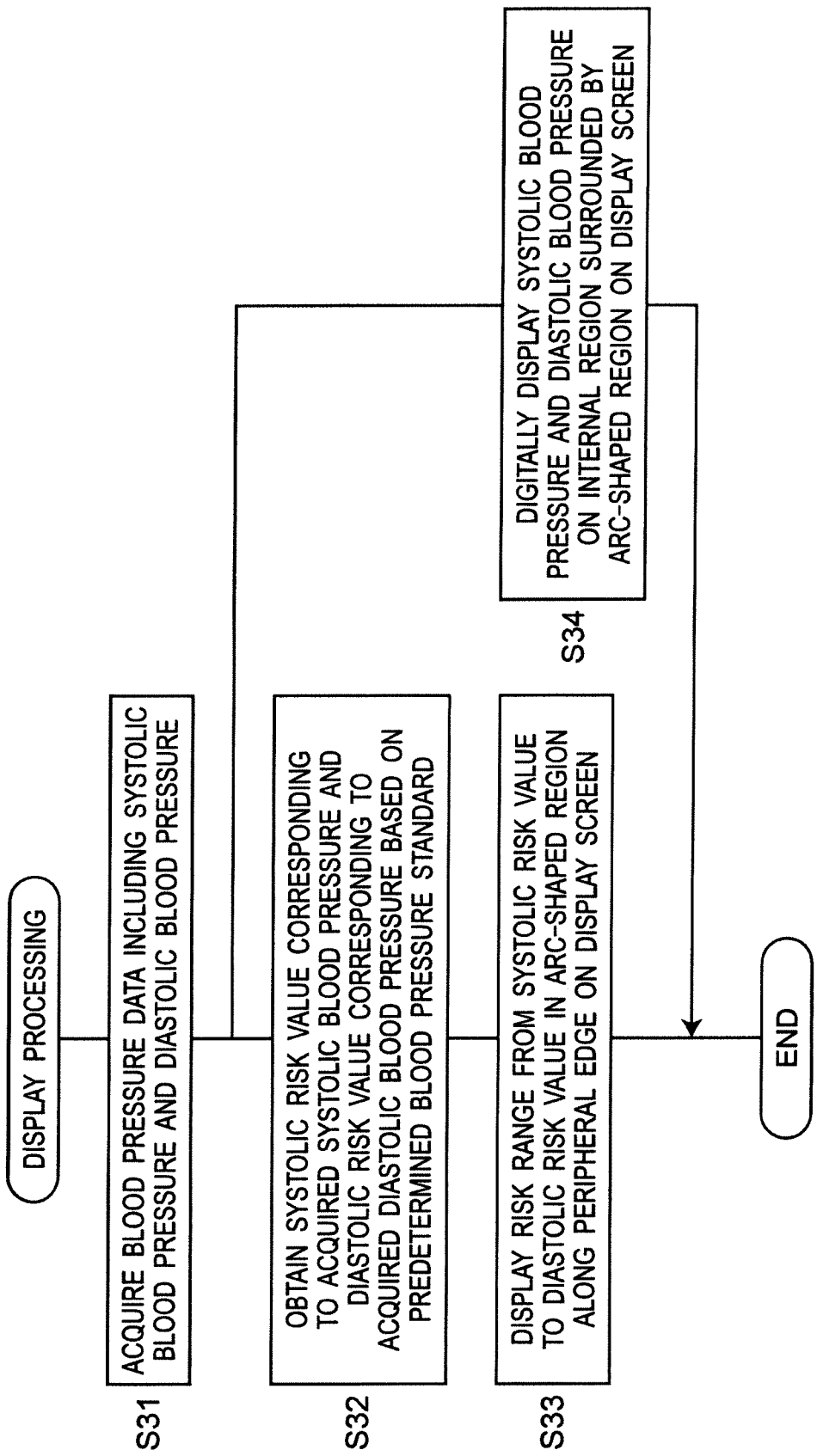
FIG. 8 is a flowchart illustrating display processing of displaying a measurement result on a display screen of a display of the sphygmomanometer as a blood-pressure-related information display method of the embodiment.

FIG. 8 is a flowchart illustrating display processing of displaying the measurement result on the display screen 500 of the display 50 as a blood-pressure-related information display method of the embodiment.

In step S31 of FIG. 8, the CPU 100 acts as a data acquisition unit, and acquires the blood pressure data including the systolic blood pressure and the diastolic blood pressure for the user (in this case, the subject). The processing corresponds to the processing of the blood pressure measurement in FIG. 4.

Subsequently, in step S32 in FIG. 8, the CPU 100 acts as a risk value calculator, and obtains the systolic risk value representing a risk corresponding to the acquired systolic blood pressure and the diastolic risk value representing a risk corresponding to the acquired diastolic blood pressure based on the AHA classification.

Figure 10:
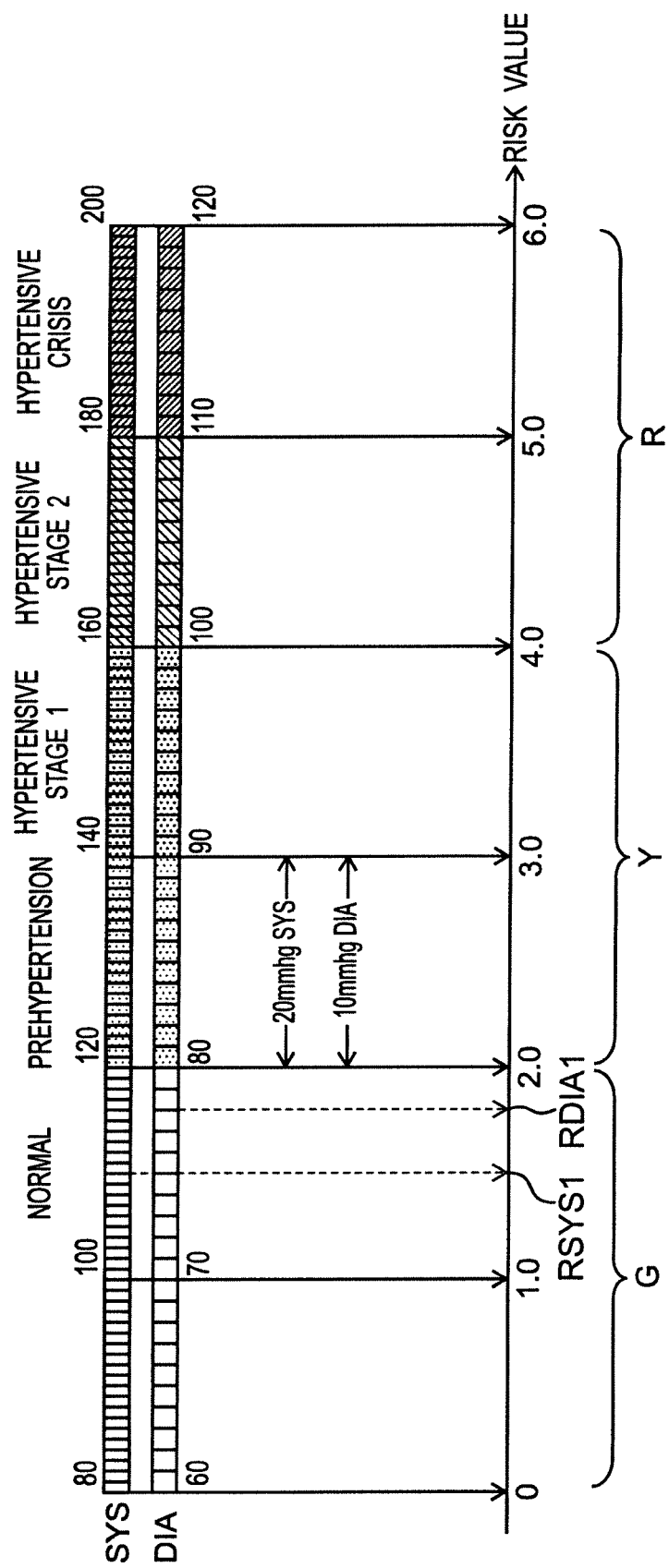
FIG. 10 is a view illustrating processing of obtaining a systolic risk value representing a risk corresponding to an acquired systolic blood pressure and a diastolic risk value representing a risk corresponding to an acquired diastolic blood pressure.

Specifically, as illustrated in FIG. 10, in this example, risk values from 0 to 6.0 are correlated with each of the acquired systolic blood pressure SYS and the acquired diastolic blood pressure DIA. For example, as indicated by a broken line in FIG. 10, when the acquired systolic blood pressure SYS is 110, 1.5 (indicated by a symbol RSYS1) is correlated as the systolic risk value. When the acquired diastolic blood pressure DIA is 78, 1.8 (indicated by a sign RDIA1) is correlated as the diastolic risk value.

More specifically, when the systolic blood pressure SYS is less than 80 mmHg, zero is correlated as the systolic risk value. When the systolic blood pressure SYS is 100 mmHg, 1.0 is correlated as the systolic risk value. When the systolic blood pressure SYS is 120 mmHg, 2.0 is correlated as the systolic risk value. When the systolic blood pressure SYS is 140 mmHg, 3.0 is correlated as the systolic risk value. When the systolic blood pressure SYS is 160 mmHg, 4.0 is correlated as the systolic risk value. When the systolic blood pressure SYS is 180 mmHg, 5.0 is correlated as the systolic risk value. When the systolic blood pressure SYS is higher than or equal to 200 mmHg, 6.0 is correlated as the systolic risk value. That is, the systolic risk value is increased by one as the systolic blood pressure SYS is increased by 20 mmHg. Within the range of each 20 mmHg of the systolic blood pressure SYS, the systolic risk value is increased by 0.1 as the systolic blood pressure SYS is increased by 2 mmHg.

Similarly, when the diastolic blood pressure DIA is less than 60 mmHg, zero is correlated as the diastolic risk value. When the diastolic blood pressure DIA is 70 mmHg, 1.0 is correlated as the diastolic risk value. When the diastolic blood pressure DIA is 80 mmHg, 2.0 is correlated as the diastolic risk value. When the diastolic blood pressure DIA is 90 mmHg, 3.0 is correlated as the diastolic risk value. When the diastolic blood pressure DIA is 100 mmHg, 4.0 is correlated as the diastolic risk value. When the diastolic blood pressure DIA is 110 mmHg, 5.0 is correlated as the diastolic risk value. When the diastolic blood pressure DIA is higher than or equal to 120 mmHg, 6.0 is correlated as the diastolic risk value. That is, the diastolic risk value is increased by one as the diastolic blood pressure DIA is increased by 10 mmHg. Within the range of each 10 mmHg of diastolic blood pressure DIA, the diastolic risk value is increased by 0.1 as the diastolic blood pressure DIA is increased by 1 mmHg.

In this example, for each of the systolic risk value and the diastolic risk value, the risk value ranging from 0 to 1.9 belongs to the first risk stage 511 to which the green G in FIG. 11 is attached, the risk value ranging from 2.0 to 3.9 belongs to the second risk stage 512 to which the yellow Y in FIG. 11 is attached, and the risk value ranging from 4.0 to 6.0 belong to the third risk stage 513 to which the red R in FIG. 11 is attached.

Subsequently, in step S33 in FIG. 8, the CPU 100 acts as a display processor, and performs processing of displaying a risk range from the systolic risk value to the diastolic risk value on the arc-shaped region 510 along the circumferential edge 500p on the display screen 500. Consequently, a continuous belt-shaped region (to be described below) is displayed as the risk range on the display screen 500. In each of the following examples, the systolic risk value is represented as RSYS1, RSYS2, . . . , and the diastolic risk value is represented as RDIA1, RDIA2, As a first example, in step S31 of FIG. 8, it is assumed that the obtained systolic blood pressure SYS is 110 mmHg and that the obtained diastolic blood pressure DIA is 78 mmHg. In this case, in step S32 of FIG. 8, as described above, the systolic risk value becomes RSYS1=1.5, and the diastolic risk value becomes RDIA1=1.8. At this point, in step S33 of FIG. 8, in order to indicate a risk range X1 from the systolic risk value RSYS1 to the diastolic risk value RDIA1, a continuous belt-shaped region X1i is displayed in the arc-shaped region 510 as illustrated in FIG. 11. The belt-shaped region X1i is wider than the range except for the risk range X1 in the arc-shaped region 510, and is highlighted. Thus, the user can intuitively recognize the risk range X1 in the arc-shaped region 510. In this example, both the systolic risk value RSYS1 and the diastolic risk value RDIA1 belong to the first risk stage 511, and the entire risk range X1 is included in the first risk stage 511. Accordingly, the green G is attached to the entire region of the belt-shaped region X1i. Thus, the user can intuitively recognize the risk stage of the blood pressure.

Figure 12:
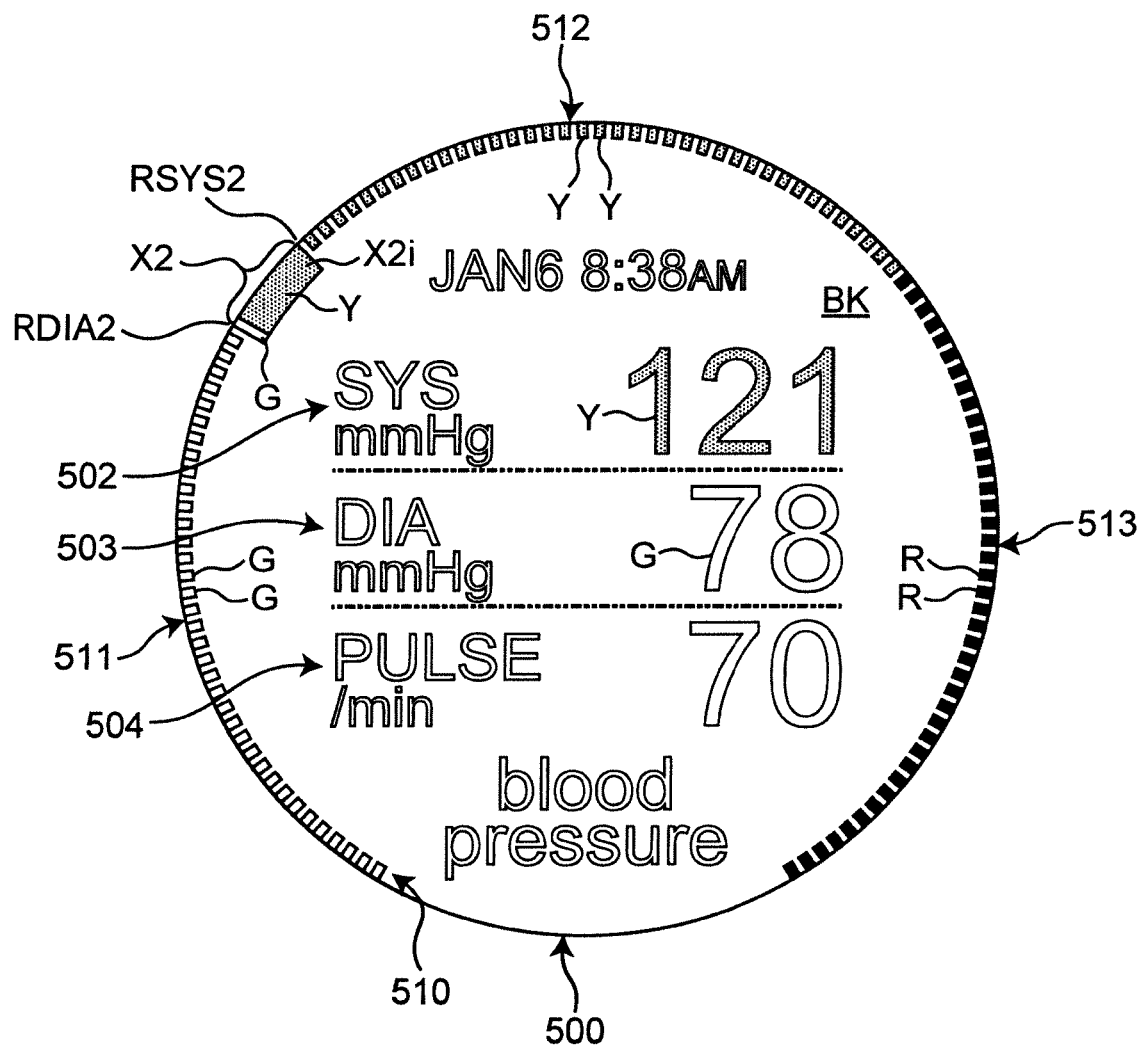
FIG. 12 is a view illustrating a second example of the blood pressure risk display by the flowchart in FIG. 8.

As a second example, in step S31 of FIG. 8, it is assumed that the acquired systolic blood pressure SYS is 121 mmHg and that the acquired diastolic blood pressure DIA is 78 mmHg. In this case, in step S32 of FIG. 8, the systolic risk value becomes RSYS2=2.0, and the diastolic risk value becomes RDIA2=1.8. That is, RDIA2<RSYS2 is obtained. At this point, in step S33 of FIG. 8, in order to indicate a risk range X2 from the systolic risk value RSYS2 to the diastolic risk value RDIA2, a continuous belt-shaped region X2i is displayed in the arc-shaped region 510 as illustrated in FIG. 12. Similarly to the belt-shaped region X1i, the belt-shaped region X2i is wider than the range except for the risk range X2 in the arc-shaped region 510, and is highlighted. Thus, the user can intuitively recognize the risk range X2 in the arc-shaped region 510. In this example, the systolic risk value RSYS2 belongs to the second risk stage 512, and the diastolic risk value RDIA2 belongs to the first risk stage 511, so that the risk range X2 straddles two stages of the first risk stage 511 and the second risk stage 512. Accordingly, the belt-shaped region X2i is color-coded into the green G and the yellow Y. Thus, the user can intuitively recognize the risk stage of the blood pressure.

Figure 13:
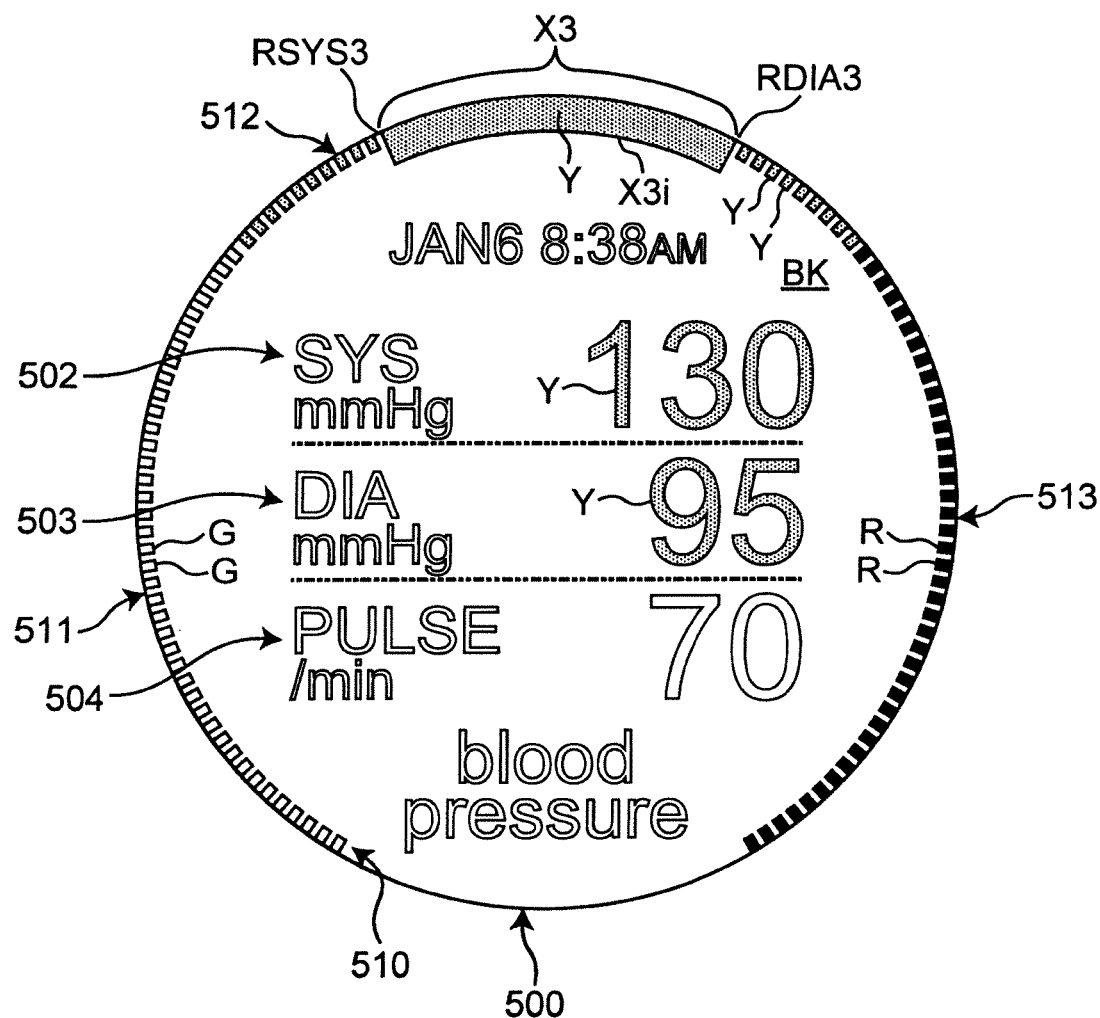
FIG. 13 is a view illustrating a third example of the blood pressure risk display by the flowchart in FIG. 8.

As a third example, in step S31 of FIG. 8, it is assumed that the acquired systolic blood pressure SYS is 130 mmHg and that the acquired diastolic blood pressure DIA is 95 mmHg. In this case, in step S32 of FIG. 8, the systolic risk value becomes RSYS3=2.5, and the diastolic risk value becomes RDIA3=3.5. That is, RSYS3<RDIA3 is obtained. At this point, in step S33 of FIG. 8, in order to indicate a risk range X3 from the systolic risk value RSYS3 to the diastolic risk value RDIA3, a continuous belt-shaped region X3i is displayed in the arc-shaped region 510 as illustrated in FIG. 13. Similarly to the belt-shaped regions X1i, X2i, the belt-shaped region X3i is wider than the range except for the risk range X3 in the arc-shaped region 510, and is highlighted. Thus, the user can intuitively recognize the risk range X3 in the arc-shaped region 510. In this example, both the systolic risk value RSYS3 and the diastolic risk value RDIA3 belong to the second risk stage 512, and the entire risk range X3 is included in the second risk stage 512. Accordingly, the yellow Y is attached to the entire region of the belt-shaped region X3i. Thus, the user can intuitively recognize the risk stage of the blood pressure.

Figure 14:
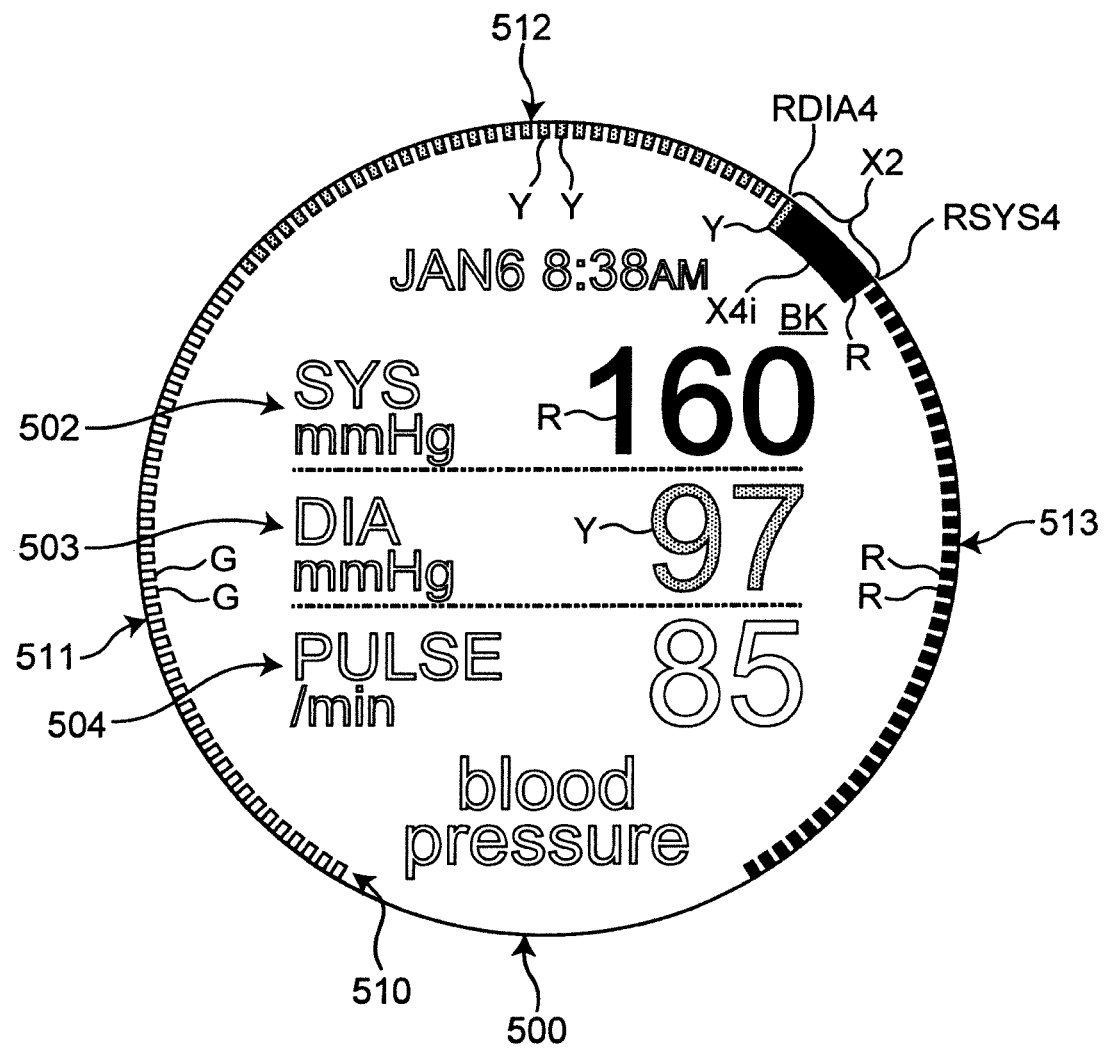
FIG. 14 is a view illustrating a fourth example of the blood pressure risk display by the flowchart in FIG. 8.

As a fourth example, in step S31 of FIG. 8, it is assumed that the acquired systolic blood pressure SYS is 160 mmHg and that the acquired diastolic blood pressure DIA is 97 mmHg. In this case, in step S32 of FIG. 8, the systolic risk value becomes RSYS4=4.0, and the diastolic risk value becomes RDIA4=3.7. That is, RDIA4<RSYS4 is obtained. At this point, in step S33 of FIG. 8, in order to indicate a risk range X4 from the systolic risk value RSYS4 to the diastolic risk value RDIA4, a continuous belt-shaped region X4i is displayed in the arc-shaped region 510 as illustrated in FIG. 14. Similarly to the belt-shaped regions X1i to X3i, the belt-shaped region X4i is wider than the range except for the risk range X4 in the arc-shaped region 510, and is highlighted. Thus, the user can intuitively recognize the risk range X4 in the arc-shaped region 510. In this example, the systolic risk value RSYS4 belongs to the third risk stage 513, and the diastolic risk value RDIA4 belongs to the second risk stage 512, so that the risk range X4 straddles two stages of the second risk stage 512 and the third risk stage 513. Accordingly, the belt-shaped region X4i is color-coded into the yellow Y and the red R. Thus, the user can intuitively recognize the risk stage of the blood pressure.

Figure 15:
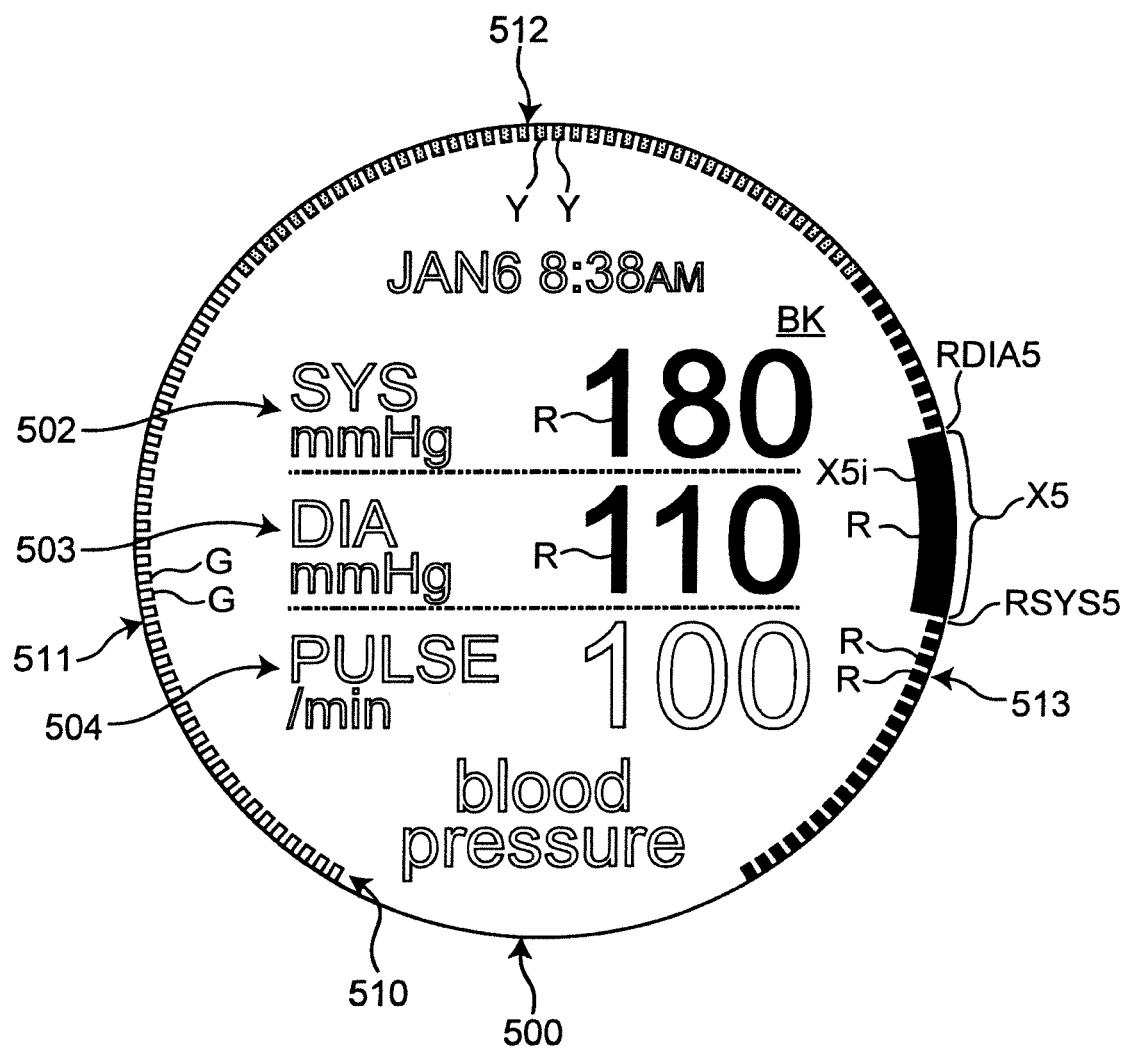
FIG. 15 is a view illustrating a fifth example of the blood pressure risk display by the flowchart in FIG. 8.

As a fifth example, in step S31 of FIG. 8, it is assumed that the acquired systolic blood pressure SYS is 180 mmHg and that the acquired diastolic blood pressure DIA is 110 mmHg. In this case, in step S32 of FIG. 8, the systolic risk value becomes RSYS5=5.0, and the diastolic risk value becomes RDIA5=4.5. That is, RDIA5<RSYS5 is obtained. At this point, in step S33 of FIG. 8, in order to indicate a risk range X5 from the systolic risk value RSYS5 to the diastolic risk value RDIA5, a continuous belt-shaped region X5i is displayed in the arc-shaped region 510 as illustrated in FIG. 15. Similarly to the belt-shaped regions X1i to X4i, the belt-shaped region X5i is wider than the range except for the risk range X5 in the arc-shaped region 510, and is highlighted. Thus, the user can intuitively recognize the risk range X5 in the arc-shaped region 510. In this example, both the systolic risk value RSYS5 and the diastolic risk value RDIA5 belong to the third risk stage 513, and the entire risk range X5 is included in the third risk stage 513. Accordingly, the red R is attached to the entire region of the belt-shaped region X5i. Thus, the user can intuitively recognize the risk stage of the blood pressure.

As a sixth example, in step S31 of FIG. 8, it is assumed that the acquired systolic blood pressure SYS is 160 mmHg and that the acquired diastolic blood pressure DIA is 78 mmHg. In this case, in step S32 of FIG. 8, the systolic risk value becomes RSYS6=4.0, and the diastolic risk value becomes RDIA6=1.8. That is, RDIA6<RSYS6 is obtained. At this point, in step S33 of FIG. 8, in order to indicate a risk range X6 from the systolic risk value RSYS6 to the diastolic risk value RDIA6, a continuous belt-shaped region X6i is displayed in the arc-shaped region 510 as illustrated in FIG. 14. Similarly to the belt-shaped regions X1i to X5i, the belt-shaped region X6i is wider than the range except for the risk range X6 in the arc-shaped region 510, and is highlighted. Thus, the user can intuitively recognize the risk range X6 in the arc-shaped region 510. In this example, the systolic risk value RSYS6 belongs to the third risk stage 513, and the diastolic risk value RDIA6 belongs to the first risk stage 511, so that the risk range X6 straddles three stages of the first risk stage 511 to the third risk stage 513. At this point, the same color as the color (in this example, red) corresponding to the highest risk stage (in this example, the third risk stage 513) of the risk range X6 is attached to an intermediate range corresponding to an intermediate risk stage (in this example, the second risk stage 512) of the risk range X6. As a result, the belt-shaped region X6i is color-coded into the green G and the red R. Thus, the user can strongly recognize that the risk range X6 spans the highest risk stage (in this example, the third risk stage 513).

In the case of displaying the first to sixth examples, the arc-shaped region 510 is a curved elongated display region, so that information related to the blood pressure of the user can be displayed in the display region having a narrow area. The user can intuitively recognize the risk range of the blood pressure by looking at the position of the risk range displayed in the arc-shaped region 510.

In this example, the CPU 100 acts as a display processor, and performs the processing in step S34 of FIG. 8 in parallel with the pieces of processing in steps S31 to S33 of FIG. 8, and digitally displays the acquired diastolic blood pressure in the diastolic blood pressure display region 503 while digitally displaying the acquired systolic blood pressure in the systolic blood pressure display region 502 in the internal region 500a surrounded by the arc-shaped region 510. The acquired pulse (/min) is digitally displayed in the pulse display region 504. Thus, the user can look at the internal region 500a to learn the digital values representing the systolic blood pressure, the diastolic blood pressure, and the pulse. The systolic blood pressure and the diastolic blood pressure are digitally displayed in the internal region 500a surrounded by the arc-shaped region 510 in the display screen 500, so that the area of the display screen 500 is effectively used.

As illustrated in FIGS. 11 to 16, the colors corresponding to the risk stages 511 to 513 to which the systolic blood pressure and the diastolic blood pressure belong are attached to the digital display of the systolic blood pressure and the digital display of the diastolic blood pressure in the systolic blood pressure display region 502 and the diastolic blood pressure display region 503. For example, the green G is attached to both the digital display of the systolic blood pressure in the systolic blood pressure display region 502 and the digital display of the diastolic blood pressure in the diastolic blood pressure display region 503 in FIG. 11. The yellow Y and the green G are attached to the digital display of the systolic blood pressure in the systolic blood pressure display region 502 and the digital display of the diastolic blood pressure in the diastolic blood pressure display region 503 in FIG. 12, respectively. The yellow Y is attached to both the digital display of the systolic blood pressure in the systolic blood pressure display region 502 and the digital display of the diastolic blood pressure in the diastolic blood pressure display region 503 in FIG. 13. The red R and the yellow Y are attached to the digital display of the systolic blood pressure in the systolic blood pressure display region 502 and the digital display of the diastolic blood pressure in the diastolic blood pressure display region 503 in FIG. 14, respectively. The red R is attached to both the digital display of the systolic blood pressure in the systolic blood pressure display region 502 and the digital display of the diastolic blood pressure in the diastolic blood pressure display region 503 in FIG. 15. The red R and the green G are attached to the digital display of the systolic blood pressure in the systolic blood pressure display region 502 and the digital display of the diastolic blood pressure in the diastolic blood pressure display region 503 in FIG. 16, respectively. Thus, by looking at the colors of the digital displays in the systolic blood pressure display region 502 and the diastolic blood pressure display region 503, the user can easily recognize which one of the systolic risk value and the diastolic risk value that define the risk ranges X1 to X6 is higher (or lower).

(First Modification)

Figure 16:
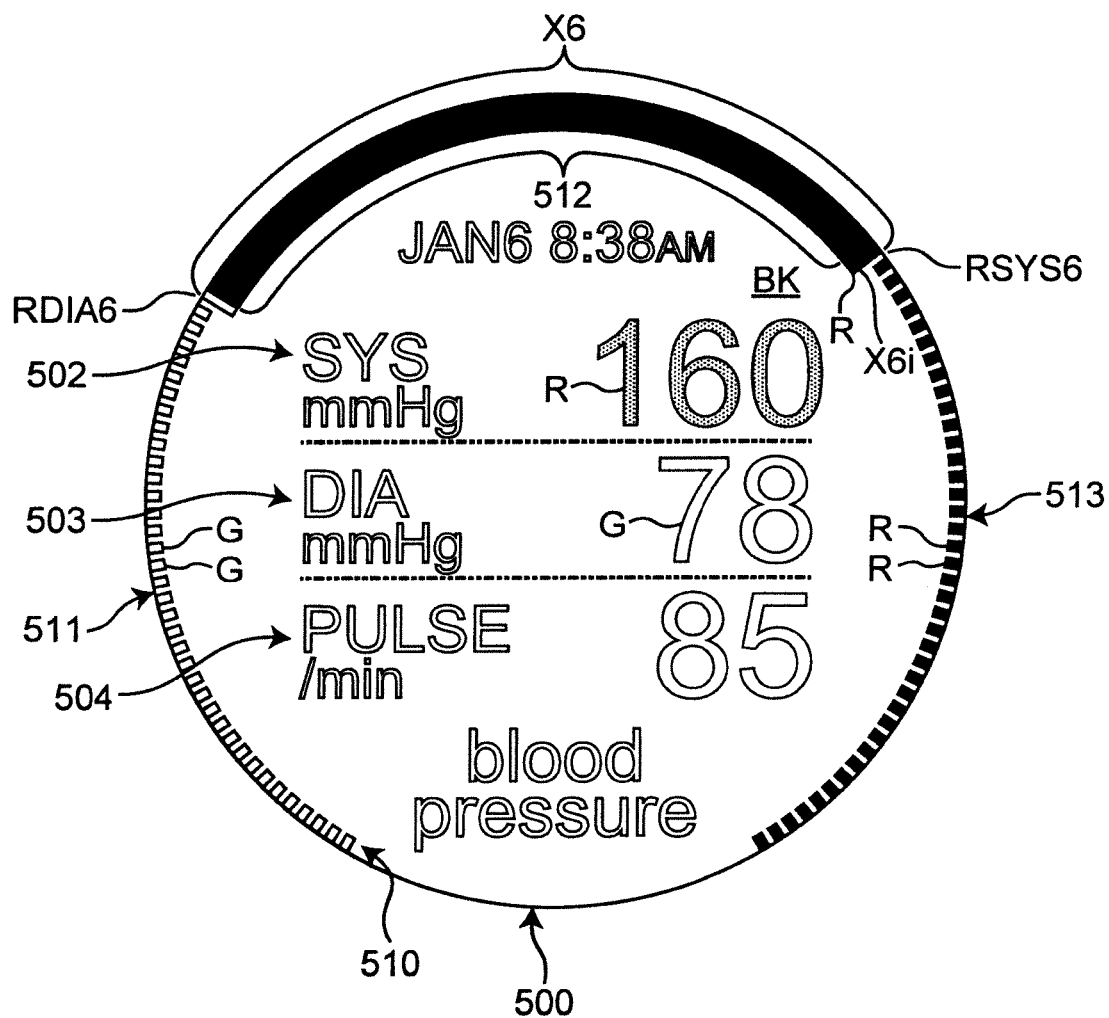
FIG. 16 is a view illustrating a sixth example of the blood pressure risk display by the flowchart in FIG. 8.
Figure 17:
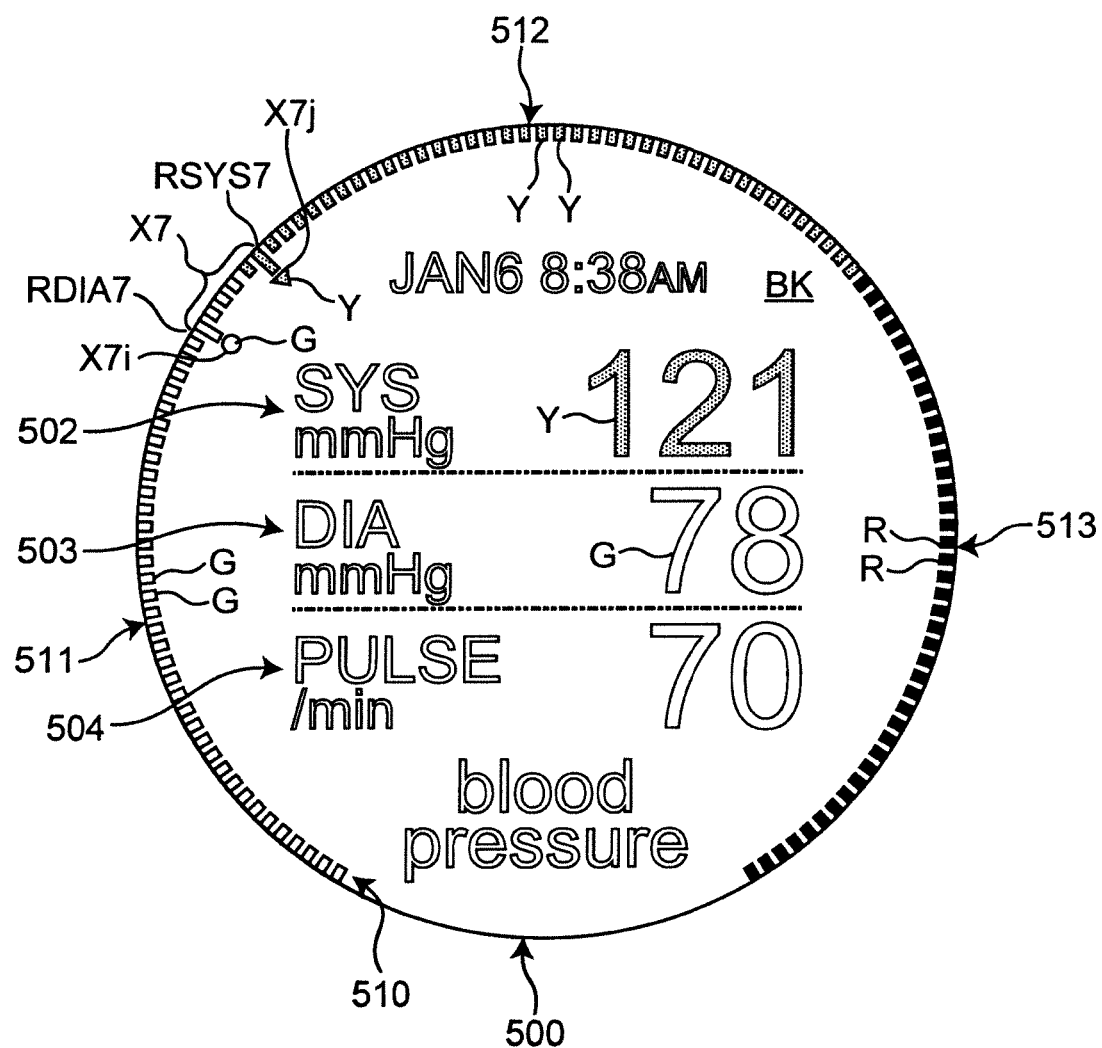
FIG. 17 is a view illustrating a modification of the blood pressure risk display.

In the examples of FIGS. 11 to 16, the risk ranges X1 to X6 are displayed as the continuous belt-shaped region. However, the present embodiment of the invention is not limited to the examples of FIGS. 11 to 16. For example, as illustrated in FIG. 17, a risk range X7 may be displayed by two marks separated from each other, the two marks being a mark X7j representing the systolic risk value and a mark X7i representing the diastolic risk value. Specifically, in this example, similarly to the example of FIG. 12, in step S31 of FIG. 8, it is assumed that the acquired systolic blood pressure SYS is 121 mmHg and that the acquired diastolic blood pressure DIA is 78 mmHg. In this case, in step S32 in FIG. 8, the systolic risk value becomes RSYS7=2.0, and the diastolic risk value becomes RDIA7=1.8. That is, RDIA7<RSYS7 is obtained. At this point, in step S33 of FIG. 8, as illustrated in FIG. 16, in order to indicate a risk range X7 from the systolic risk value RSYS7 to the diastolic risk value RDIA7, a mark X7j of a ∇ sign representing the systolic risk value and a mark X7i of a ○ sign representing the diastolic risk value are displayed on the inner circumferential side of the arc-shaped region 510. Thus, the user can intuitively recognize the risk range X7 in the arc-shaped region 510. In this example, the systolic risk value RSYS7 belongs to the second risk stage 512, and the diastolic risk value RDIA7 belongs to the first risk stage 511. Accordingly, the yellow Y is attached to the mark X7j of the ∇ sign representing the systolic risk value, and the green G is attached to the mark X7i of the ○ sign indicating the diastolic risk value. Thus, the user can intuitively recognize the risk stage of the blood pressure.

(Second Modification)

Figure 18:
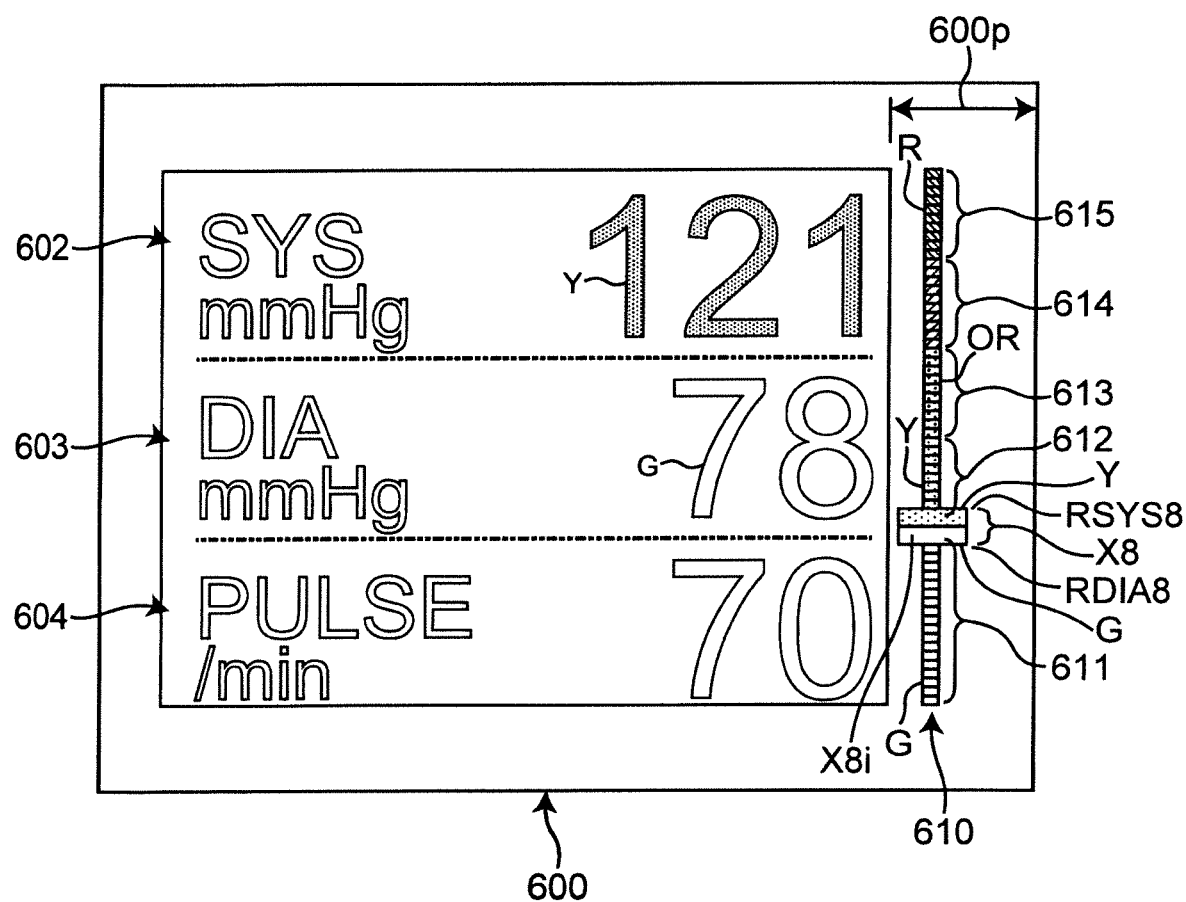
FIG. 18 is a view illustrating another modification of the blood pressure risk display.

In the examples of FIGS. 11 to 17, the display screen 500 has the circular shape, and the risk ranges X1 to X7 are displayed in the arc-shaped region 510 along the annular circumferential edge 500p. However, the present embodiment of the invention is not limited to the examples of FIGS. 11 to 17. For example, as illustrated in FIG. 18, a display screen 600 has a rectangular shape, and a column region 610 may be provided as a straight elongated display region defining a one-dimensional risk coordinate along an edge 600p of one side (in this example, the right side) of the display screen 600. In this example, a systolic blood pressure display region 602, a diastolic blood pressure display region 603, and a pulse display region 604 that cover most of the display screen 600 are provided on the left side of the column region 610. The systolic blood pressure display region 602, the diastolic blood pressure display region 603, and the pulse display region 604 correspond to the systolic blood pressure display region 502, the diastolic blood pressure display region 503, and the pulse display region 504 in FIGS. 11 to 17, respectively.

In this example, the column region 610 is divided into five stages from a first risk stage 611 to a fifth risk stage 615 based on the AHA classification. The first risk stage 611 corresponds to the "normal" category of the AHA classification. The second risk stage 612 corresponds to "prehypertension" of the AHA classification. The third risk stage 613 corresponds to "hypertension stage 1" of the AHA classification. The fourth risk stage 614 corresponds to "hypertension stage 2" of the AHA classification. The fifth risk stage 615 corresponds to "hypertensive crisis" of the AHA classification.

In this example, in the same way as illustrated in FIG. 10, the risk values from 0 to 6.0 are correlated with each of the acquired systolic blood pressure SYS and the acquired diastolic blood pressure DIA.

In the same way as illustrated in FIGS. 11 to 16, a continuous belt-shaped region X8i is displayed in the column region 610 as the risk range from the systolic risk value to the diastolic risk value. For example, in step S31 of FIG. 8, it is assumed that the acquired systolic blood pressure SYS is 121 mmHg and that the acquired diastolic blood pressure DIA is 78 mmHg. In this case, in step S32 of FIG. 8, the systolic risk value becomes RSYS 8=2.0, and the diastolic risk value becomes RDIA 8=1.8. That is, RDIA8<RSYS8 is obtained. At this point, in step S33 of FIG. 8, in order to indicate a risk range X8 from the systolic risk value RSYS8 to the diastolic risk value RDIA8, a continuous belt-shaped region X8i is displayed in the column region 610 as illustrated in FIG. 18. Similarly to the belt-shaped regions X1i to X6i, the belt-shaped region X8i is wider than the range except for the risk range X8 in the column region 610, and is highlighted. Thus, the user can intuitively recognize the risk range X8 in the column region 610. In this example, the systolic risk value RSYS8 belongs to the second risk stage 612, and the diastolic risk value RDIA8 belongs to the first risk stage 611, so that the risk range X8 straddles two stages of the first risk stage 611 and the second risk stage 612. Accordingly, the belt-shaped region X8i is color-coded into the green G and the yellow Y. Thus, the user can intuitively recognize the risk stage of the blood pressure.

A color, such as an orange OR to the red R, which intuitively indicates that a degree of warning is sequentially increased, is attached to the third risk stage 613 to the fifth risk stage 615.

Even if the risk range X8 is displayed in the straight column region 610, the user can intuitively recognize the risk range of the blood pressure by looking at the position of the risk range X8 displayed in the column region 610.

In the above embodiment, in this example, the risk values from 0 to 6.0 are correlated with each of the acquired systolic blood pressure SYS and the acquired diastolic blood pressure DIA. However, the present invention is not limited to the embodiment. The risk value only intervenes in order to correlate the acquired systolic blood pressure SYS and the acquired diastolic blood pressure DIA with the display position of the risk range in the arc-shaped region 510 or the column region 610. Another scale value such as 0 to 100 may be used as the risk value.

In the above embodiment, the display region (the arc-shaped region 510, the column region 610) defining the one-dimensional risk coordinate is divided into the risk stages of three stages or five stages. However, the present invention is not limited to the embodiment. The display region may be divided into two stages, four stages, or at least six stages. The display region may not be divided, but set to one stage. The color given to each stage is not limited to the green G, the yellow Y, the red R, and the like, but various colors may be used.

In the above embodiment, in the display region (the arc-shaped region 510, the column region 610) defining the one-dimensional risk coordinate, the belt-shaped regions X1i to X6i, X8i indicating the risk range is wider than the region (other regions) except for the risk range, and is highlighted. However, the highlighting is not limited to the embodiment. The risk range may be highlighted by displaying brighter, displaying more vividly, or blinking as compared with the range except for the risk range.

In the above embodiment, the display screen has the circular shape (display screen 500) or the rectangular shape (display screen 600). However, the present invention is not limited to the embodiment. The display screen may have various shapes such as a hexagonal shape, an octagonal shape, and a shape in which a part of a circle is cut flat.

In the above embodiment, the display region (the arc-shaped region 510, the column region 610) where the risk range is displayed and the display region (the systolic blood pressure display regions 502, 602, the diastolic blood pressure display regions 503, 603, and the like) where the systolic blood pressure, the diastolic blood pressure, and the like are digitally displayed are provided together. However, the present invention is not limited to the embodiment. Only a display region where the risk range is displayed may be provided in the display screen.

In the above embodiment, by way of example, the blood pressure data including the systolic blood pressure and the diastolic blood pressure of the subject is measured and acquired by the blood pressure measurement element mounted on the main body 10 of the sphygmomanometer 1 in order to display the blood pressure risk on the display screen of the display 50. However, the present invention is not limited to the embodiment. For example, the blood pressure data including the systolic blood pressure and the diastolic blood pressure of the subject is input from the outside of the sphygmomanometer 1 through the communicator 59, and the blood pressure risk may be displayed on the display screen of the display 50 based on the blood pressure data. Alternatively, conversely, the blood pressure data including the systolic blood pressure and the diastolic blood pressure measured by the blood pressure measurement element mounted on the main body 10 of the sphygmomanometer 1 is output to an external substantial computer device such as a smartphone through the communicator 59, and the computer device may perform the above blood-pressure-related information display method to display the blood pressure risk on the display screen of the computer device.

A program causing a computer to perform the blood-pressure-related information display method according to the above embodiment can also be provided. The program is non-transitory recorded in a computer-readable recording medium, such as a flexible disk, a compact disk-read only memory (CD-ROM), a ROM, a RAM and a memory card, which is attached to the computer, and the program can be provided as a program product. Alternatively, the program can be provided while non-temporarily recorded in a recording medium such as a hard disk built in the computer. The program can also be provided by download through a network.

The above embodiments are illustrative only, and various modifications can be made without departing from the scope of the present invention. The plurality of embodiments described above can be made independently, and the embodiments can also be combined. Although various features in different embodiments can independently be established, the features in different embodiments can also be combined.

According to a blood-pressure-related information display device of the present embodiment, the blood-pressure-related information display device that displays information related to a blood pressure of a subject on a display screen, includes:

a data acquisition unit to acquire blood pressure data including a systolic blood pressure and a diastolic blood pressure for the subject;

a risk value calculator to obtain a systolic risk value representing a risk corresponding to the acquired systolic blood pressure and a diastolic risk value representing a risk corresponding to the acquired diastolic blood pressure based on a predetermined blood pressure standard; and a display processor to perform processing of displaying a risk range from the systolic risk value to the diastolic risk value in a curved or straight elongated display region defining a one-dimensional risk coordinate in the display screen.

In the present description, the "information related to the blood pressure of the subject" broadly means the blood-pressure-related information including information representing a risk related to the blood pressure in addition to the blood pressure value (systolic blood pressure (maximum blood pressure) and the diastolic blood pressure (minimum blood pressure)).

For example, the "predetermined blood pressure standard" means a classification published by World Health Organization (WHO)/International Hypertension Society (ISH), a classification published by American Joint Committee on Hypertension (JNC)/American Heart Association (AHA), and "High blood pressure treatment guidelines 2014" published by Japanese Society of Hypertension.

In a blood-pressure-related information display device of the present embodiment, a data acquisition unit acquires blood pressure data including a systolic blood pressure and a diastolic blood pressure for a subject. A risk value calculator obtains a systolic risk value representing a risk corresponding to the acquired systolic blood pressure and a diastolic risk value representing a risk corresponding to the acquired diastolic blood pressure based on a predetermined blood pressure standard. A display processor performs processing of displaying a risk range from the systolic risk value to the diastolic risk value in a curved or straight elongated display region defining a one-dimensional risk coordinate in the display screen. In this case, because the display region is a curved or straight elongated display region, information related to the blood pressure of the subject can be displayed in the display region having a narrow area. Additionally, a user (typically the user is the subject, but may be a person except for the subject) can intuitively recognize the risk range of the blood pressure by looking at a position of the risk range displayed in the display region.

The data acquisition unit may measure and acquire blood pressure data, or acquire the blood pressure data from the outside of the device, for example, through a network.

In the blood-pressure-related information display device of the embodiment, the display processor displays the risk range in the display region as a continuous belt-shaped region.

In the blood-pressure-related information display device of the embodiment, the display processor displays the risk range in the display region as a continuous belt-shaped region. Thus, the user can more intuitively recognize the risk range in the display region.

In the blood-pressure-related information display device of the embodiment, the display region is divided into a plurality of risk stages according to the blood pressure standard, and the display processor color-codes and displays the risk range in the display region according to the risk stage.

In the blood-pressure-related information display device of the embodiment, the display region is divided into a plurality of stages according to the blood pressure standard. The display processor color-codes and displays the risk range in the display region according to the risk stage. Thus, the user can more intuitively recognize the risk stage of the blood pressure.

In the blood-pressure-related information display device of the embodiment, the display region is divided into at least three risk stages according to the blood pressure standard, and when the risk range in the display region straddles at least three risk stages, the display processor attaches a color identical to a color corresponding to the highest risk stage in the risk range to an intermediate range corresponding to an intermediate risk stage in the risk range.

In the blood-pressure-related information display device of the embodiment, when the risk range in the display region straddles at least three risk stages, the display processor attaches a color identical to a color corresponding to the highest risk stage in the risk range to an intermediate range corresponding to an intermediate risk stage in the risk range. Thus, the user can strongly recognize that the risk range spans the highest risk stage.

In the blood-pressure-related information display device of the embodiment, the display processor highlights the risk range in the display region as compared with a range except for the risk range in the display region.

In the present description, the "highlighting" means that the risk range is displayed wider, brighter, more vividly, or blinked as compared with the range except for the risk range.

In the blood-pressure-related information display device of the embodiment, the display processor highlights the risk range in the display region as compared with a range except for the risk range in the display region. Thus, the user can more easily and more intuitively recognize the risk range.

In the blood-pressure-related information display device of the embodiment, the display processor digitally displays the acquired systolic blood pressure and the acquired diastolic blood pressure in the display screen.

In the blood-pressure-related information display device of the embodiment, the acquired systolic blood pressure and the acquired diastolic blood pressure are digitally displayed in the display screen in addition to the display (that is, analog display) of the risk range. Thus, the user can learn the digital values representing the systolic blood pressure and the diastolic blood pressure by looking at the display screen.

In the blood-pressure-related information display device of the embodiment, the display region is an arc-shaped region along a peripheral edge of the display screen, and the acquired systolic blood pressure and the acquired diastolic blood pressure are digitally displayed in an internal region surrounded by the arc-shaped region of the display screen.

In the blood-pressure-related information display device of the embodiment, the acquired systolic blood pressure and the acquired diastolic blood pressure are digitally displayed in an internal region surrounded by the arc-shaped region in the display screen. Thus, the area of the display screen is effectively used.

In the blood-pressure-related information display device of the embodiment, the display processor attaches a color corresponding to the risk stage to which the systolic risk value and the diastolic risk value belong to digital display of the acquired systolic blood pressure and digital display of the acquired diastolic blood pressure.

In the blood-pressure-related information display device of the embodiment, the display processor attaches a color corresponding to the risk stage to which the systolic risk value and the diastolic risk value belong to digital display of the acquired systolic blood pressure and digital display of the acquired diastolic blood pressure. Thus, the user can easily recognize which one of the systolic risk value and the diastolic risk value that define the risk range is higher (or lower) by looking at the colors of the digital displays.

In the blood-pressure-related information display device of the embodiment, the data acquisition unit, the risk value calculator, and the display processor are integrally mounted on a main body including the display screen.

In the blood-pressure-related information display device of the embodiment, the data acquisition unit, the risk value calculator, and the display processor are integrally mounted on a main body including the display screen. Thus, the blood-pressure-related information display device can be applied to a sphygmomanometer of a type in which a main body including a pump and a blood pressure measurement cuff are integrated. In the display screen of the main body, the information related to the blood pressure of the subject can be displayed in the display region having the narrow area.

According to another aspect of the present embodiment, a blood-pressure-related information display method for displaying information related to a blood pressure of a subject on a display screen, the blood-pressure-related information display method, includes:

acquiring blood pressure data including a systolic blood pressure and a diastolic blood pressure for the subject;

obtaining a systolic risk value representing a risk corresponding to the acquired systolic blood pressure and a diastolic risk value representing a risk corresponding to the acquired diastolic blood pressure based on a predetermined blood pressure standard; and performing processing of displaying a risk range from the systolic risk value to the diastolic risk value in a curved or straight elongated display region defining a one-dimensional risk coordinate in the display screen.

In a blood-pressure-related information display method of the present embodiment, blood pressure data including a systolic blood pressure and a diastolic blood pressure is acquired for a subject. A systolic risk value representing a risk corresponding to the acquired systolic blood pressure and a diastolic risk value representing a risk corresponding to the acquired diastolic blood pressure are obtained based on a predetermined blood pressure standard. Processing of displaying a risk range from the systolic risk value to the diastolic risk value in a curved or straight elongated display region forming a one-dimensional risk coordinate defined in the display screen is performed. In this case, because the display region is a curved or straight elongated display region, information related to the blood pressure of the subject can be displayed in the display region having a narrow area. The user can intuitively recognize the risk range in the display region by looking at the position of the risk range displayed in the display region.

According to another aspect of the present embodiment, a program causes a computer to perform the blood-pressure-related information display method.

According to the program of the present embodiment, a computer can perform the blood-pressure-related information display method.

As apparent from the above, according to the blood-pressure-related information display device and blood-pressure-related information display method of the present embodiment, the information related to the blood pressure of the subject can be displayed in the display region having the narrow area.

According to the program of the present embodiment, the computer can perform the blood-pressure-related information display method.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

What is claimed is:

1. A blood-pressure-related information display device that displays information related to a blood pressure of a subject on a display screen, the blood-pressure-related information display device comprising:

a data acquisition unit configured to acquire blood pressure data including a systolic blood pressure and a diastolic blood pressure for the subject;

a risk value calculator configured to convert the acquired systolic blood pressure to a systolic risk value and to convert the acquired diastolic blood pressure to a diastolic risk value; and a display processor configured to perform processing of:
(i) displaying a curved or straight, elongated, one-dimensional risk value scale, wherein both the systolic risk value and the diastolic risk value are plotted on the same risk value scale;
(ii) displaying a risk range extending from the systolic risk value to the diastolic risk value on the same risk value scale; and
(iii) digitally displaying the acquired systolic blood pressure and the acquired diastolic blood pressure in the display screen, wherein the systolic risk value is a value between a predetermined low value and a predetermined high value along the risk value scale and the diastolic risk value is a value between the predetermined low value and the predetermined high value along the risk value scale.

2. The blood-pressure-related information display device according to claim 1, further comprising a display region, wherein the display processor displays the risk range in the display region as a continuous belt-shaped region.

3. The blood-pressure-related information display device according to claim 2, wherein
the display region is divided into a plurality of risk stages according to a predetermined blood pressure standard, and
the display processor color-codes and displays the risk range in the display region according to the risk stage.

4. The blood-pressure-related information display device according to claim 3, wherein
the display region is divided into three risk stages, consisting of a lowest risk stage, an intermediate risk stage, and a highest risk stage according to the predetermined blood pressure standard, and
when the risk range extends across a portion of the lowest risk stage, an entire portion of the intermediate risk stage and a portion of the highest risk stage,
the display processor color-codes and displays a portion of the risk range that is over the entire intermediate risk stage in a color corresponding to the highest risk stage.

5. The blood-pressure-related information display device according to claim 3, wherein
the display region is divided into at least three risk stages according to the predetermined blood pressure standard, and
when the risk range extends across three risk stages of the at least three risk stages,
the display processor color-codes and displays a portion of the risk range that is over an intermediate risk stage of the three risk stages in a color corresponding to a highest risk stage.

6. The blood-pressure-related information display device according to claim 1, wherein the display processor highlights the risk range in a display region and does not highlight another range different from the risk range in the display region.

7. The blood-pressure-related information display device according to claim 1, further comprising:
a display region
wherein the display region, in which the risk range is displayed, is an arc-shaped region along a peripheral edge of the display screen, and
the acquired systolic blood pressure and the acquired diastolic blood pressure are digitally displayed in an internal region surrounded by the arc-shaped region of the display screen.

8. The blood-pressure-related information display device according to claim 7, wherein the display processor digitally displays the acquired systolic risk value on the display screen in a color corresponding to a risk stage to which the systolic risk value belongs, and
the display processor digitally displays the acquired diastolic risk value on the display screen in a color corresponding to a risk stage to which the diastolic value belongs.

9. The blood-pressure-related information display device according to claim 1, wherein the display processor digitally displays the acquired systolic risk value on the display screen in a color corresponding to a risk stage to which the systolic risk value belongs, and
the display processor digitally displays the acquired diastolic risk value on the display screen in a color corresponding to a risk stage to which the diastolic risk value belongs.

10. The blood-pressure-related information display device according to claim 1, wherein the data acquisition unit, the risk value calculator, and the display processor are integrally mounted on a main body including the display screen.

11. A blood-pressure-related information display method for displaying information related to a blood pressure of a subject on a display screen, the blood-pressure-related information display method comprising:
acquiring blood pressure data including a systolic blood pressure and a diastolic blood pressure for the subject;
converting the acquired systolic blood pressure to a systolic risk value and converting the acquired diastolic blood pressure to a diastolic risk value;
performing processing of:
(i) displaying a curved or straight, elongated, one-dimensional risk value scale, wherein both the systolic risk value and the diastolic risk value are plotted on the same risk value scale;
(ii) displaying a risk range extending from the systolic risk value to the diastolic risk value on the same risk value scale; and
(iii) digitally displaying the acquired systolic blood pressure and the acquired diastolic blood pressure in the display screen,
wherein the systolic risk value is a value between a predetermined low value and a predetermined high value along the risk value scale and
the diastolic risk value is a value between the predetermined low value and the predetermined high value along the risk value scale.

12. A non-transitory computer-readable recording medium storing program which, when executed by a computer, causes the computer to perform a blood-pressure-related information display method for displaying information related to a blood pressure of a subject on a display screen, the blood-pressure-related information display method comprising:
acquiring blood pressure data including a systolic blood pressure and a diastolic blood pressure for the subject;
converting the acquired systolic blood pressure to a systolic risk value and converting the acquired diastolic blood pressure to a diastolic risk value;
performing processing of:
(i) displaying a curved or straight, elongated, one-dimensional risk value scale, wherein both the systolic risk value and the diastolic risk value are plotted on the same risk value scale;
(ii) displaying a risk range extending from the systolic risk value to the diastolic risk value on the same risk value scale; and
(iii) digitally displaying the acquired systolic blood pressure and the acquired diastolic blood pressure in the display screen,
wherein the systolic risk value is a value between a predetermined low value and a predetermined high value along the risk value scale and
the diastolic risk value is a value between the predetermined low value and the predetermined high value along the risk value scale.

* * * * *